US008620048B2

(12) United States Patent
Nakano et al.

(10) Patent No.: US 8,620,048 B2
(45) Date of Patent: Dec. 31, 2013

(54) IMAGE PROCESSING APPARATUS, IMAGE PROCESSING SYSTEM, IMAGE PROCESSING METHOD, AND IMAGE PROCESSING COMPUTER PROGRAM

(75) Inventors: Yuta Nakano, Juan-les-pins (FR); Kenji Morita, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/583,116

(22) PCT Filed: Mar. 11, 2011

(86) PCT No.: PCT/JP2011/001457
§ 371 (c)(1),
(2), (4) Date: Sep. 6, 2012

(87) PCT Pub. No.: WO2011/114685
PCT Pub. Date: Sep. 22, 2011

(65) Prior Publication Data
US 2013/0004046 A1  Jan. 3, 2013

(30) Foreign Application Priority Data
Mar. 19, 2010 (JP) ................. 2010-064755

(51) Int. Cl.
*G06K 9/00* (2006.01)
*A61B 3/10* (2006.01)
(52) U.S. Cl.
USPC ............................ 382/128; 382/275; 351/212

(58) Field of Classification Search
USPC ......... 382/100, 103, 106, 117, 128–134, 155, 382/162, 173, 181, 199, 220, 232, 254, 274, 382/275, 276, 305, 312; 600/425; 345/440; 351/206, 212
See application file for complete search history.

(56) References Cited

U.S. PATENT DOCUMENTS

| 6,276,798 | B1 * | 8/2001 | Gil et al. ........................ 351/206 |
| 7,905,596 | B2 * | 3/2011 | Aoki et al. ..................... 351/206 |
| 8,408,704 | B2 * | 4/2013 | Tomidokoro et al. ......... 351/206 |
| 2009/0163898 | A1 | 6/2009 | Gertner |
| 2010/0202677 | A1 * | 8/2010 | Imamura et al. .............. 382/131 |
| 2010/0220914 | A1 * | 9/2010 | Iwase et al. ................... 382/131 |
| 2010/0278402 | A1 * | 11/2010 | Everett et al. ................. 382/128 |

FOREIGN PATENT DOCUMENTS

| JP | 2008-073099 A | 4/2008 |
| WO | 2007/084748 A2 | 7/2007 |
| WO | 2007/133964 A2 | 11/2007 |

* cited by examiner

*Primary Examiner* — Seyed Azarian
(74) *Attorney, Agent, or Firm* — Canon U.S.A., Inc., IP Division

(57) ABSTRACT

An image processing apparatus according to the present invention includes an acquisition unit configured to acquire a tomography image of a target to be captured, a detection unit configured to detect layer boundaries of a plurality of layers sequentially positioned in the depth direction from the acquired tomography image, and a determination unit configured to determine a structure of the target to be captured according to the number of the detected layer boundaries.

20 Claims, 20 Drawing Sheets

IMAGE PROCESSING APPARATUS, IMAGE PROCESSING SYSTEM, IMAGE PROCESSING METHOD, AND IMAGE PROCESSING COMPUTER PROGRAM

TECHNICAL FIELD

The present invention relates to an image processing apparatus, an image processing system, an image processing method, and an image processing computer program, which can be used to identify a layer structure based on a tomography image.

BACKGROUND ART

The eye examination is widely known as an effective method capable of diagnosing at early timing the type of a disease that may lead to a lifestyle related disease or blindness. An optical coherence tomography (OCT) or a comparable tomography imaging apparatus enables an eye doctor or any other specialist to observe a three-dimensional state of internal retinal layers.

For example, the retina has a layer structure that is composed of a plurality of layers. Information relating to thickness of each layer etc. is usable as an objective index that indicates the stage of a disease.

In order to observe the retinal layer structure or to obtain the index, a technique capable of analyzing a tomography image of retinal layers is used to identify the layer structure.

A conventional method discussed in Japanese Patent Application Laid-Open No. 2008-73099 includes performing preprocessing (e.g., gradation conversion) on a tomography image and detecting an edge from the processed image in the depth direction. The above-described conventional method further includes identifying the position of a layer boundary based on the position of a detected edge.

The layer structure of retinal layers includes a locally deformed region where a characteristic part (e.g., optic disc or macula) is present. Further, if the layer structure includes a blood vessel or a leucoma, signal light may not reach an underlying region beneath the above-described portions and a target layer boundary to be identified may not be included in a captured image.

However, the conventional processing discussed in Japanese Patent Application Laid-Open No. 2008-73099 does not take the above-described local change in the layer structure into consideration. Therefore, the layer structure identification with the method may be failed.

CITATION LIST

Patent Literature

PTL 1: Japanese Patent Application Laid-Open No. 2008-73099

SUMMARY OF INVENTION

According to an aspect of the present invention, an image processing apparatus includes an acquisition unit configured to acquire a tomography image of a target to be captured, a detection unit configured to detect layer boundaries of a plurality of layers sequentially positioned in the depth direction from the acquired tomography image, and a determination unit configured to determine a structure of the target to be captured according to the number of the detected layer boundaries.

According to the image processing apparatus having the above-described configuration, it is possible to deal with the difference of the layer structure and reduce errors in determining the structure since the determination about the structure can be made according to a number of layer boundaries.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

FIG. 5A schematically illustrates an example image including edges enhanced in the direction from the lower pixel value side to the higher pixel value side.

FIG. 5B schematically illustrates an example image including edges enhanced in the direction from the higher pixel value side to the lower pixel value side.

DESCRIPTION OF EMBODIMENTS

Various exemplary embodiments, features, and aspects of the invention will be described in detail below with reference to the drawings.

An image processing system 100 according to a first exemplary embodiment includes an image processing apparatus 101 that can identify the position and the type of a layer structure based on a tomography image of a retina received from a tomography image acquisition apparatus 102.

In this case, the image processing apparatus 101 identify layer boundaries by applying template information to each portion having a unique structure in the tomography image.

Further, the image processing apparatus 101 interpolates an unidentified layer boundary portion, if it was not identified by the applied template information, with reference to the position of the layer boundary already identified based on the template information.

In this case, the image processing apparatus 101 sets a range that can be presumed to include the unidentified layer boundary portion based on the position of the already identified layer boundary. Then, the image processing apparatus 101 identifies a target layer boundary based on a luminance change value in the set range.

An example configuration of the image processing system 100 and example processing that can be performed by the image processing system 100 are described below.

Figure 1:
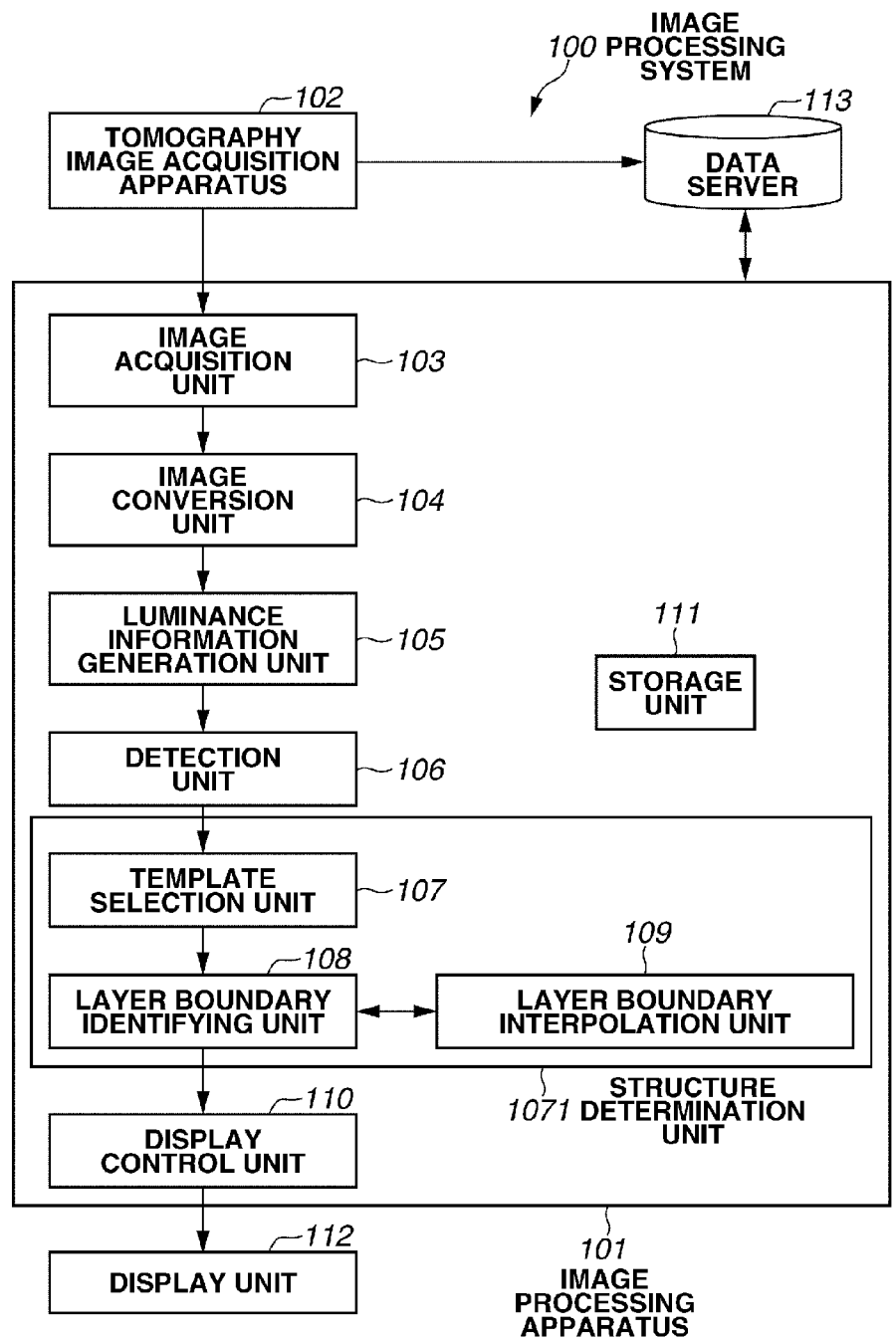
FIG. 1 illustrates an example configuration of an image processing system according to the first exemplary embodiment of the present invention.

An example configuration of the image processing system 100 is described below with reference to FIG. 1. The image processing apparatus 101 is, for example, a computer. The image processing apparatus 101 includes an image acquisition unit 103, an image conversion unit 104, a luminance information generation unit 105, a detection unit 106, a structure determination unit 1071, a display control unit 110, and a storage unit 111.

Each of the above-described functional blocks can be constituted by an electric circuit. Alternatively, the image processing apparatus 101 may have a hardware configuration and a software configuration that are cooperatively operable as each of the above-described functional blocks.

As an example software configuration (although not illustrated in the drawing), the image processing apparatus 101 can include a central processing unit (CPU), a read only memory (ROM), and a random access memory (RAM). For example, to realize processing described in FIG. 4, FIG. 7, and FIG. 11, the CPU can execute a program or programs loaded into the RAM from the ROM. In this manner, the hardware and software configuration of the computer can cooperatively realize the present invention.

The tomography image acquisition apparatus 102 is, for example, an optical coherence tomography imaging apparatus (optical coherence tomography imaging unit) whose operation is based on the principle of Optical Coherence Tomography. The tomography image acquisition apparatus 102 is described below in more detail.

The image acquisition unit 103 of the image processing apparatus 101 acquires a tomography image from the tomography image acquisition apparatus 102. The tomography image obtainable from the tomography image acquisition apparatus 102 is a tomography image of a three-dimensional region of a retina that can be obtained by scanning a predetermined two-dimensional area on a retinal surface.

The tomography image represents an internal layer structure of the retina. The tomography image can be acquired as a plurality of two-dimensional tomography images (B-scan images) or can be acquired as one-dimensional images (A-scan images) obtained at a plurality of positions on the retinal surface irradiated with signal light. Alternatively, the tomography image may be acquired as three-dimensional volume data that can be generated based on A-scan images.

The image conversion unit 104 can use a Sobel filter and a median filter to obtain images converted from an input image. More specifically, when the Sobel filter is applied to an acquired tomography image, a Sobel image having enhanced edges can be obtained. When the median filter is applied to an acquired tomography image, a smoothed image can be generated as a median image.

The luminance information generation unit 105 can generate, from the Sobel image and the median image, information indicating a relationship between luminance value and depth directional position at a predetermined position in the horizontal direction. More specifically, the information to be generated by the luminance information generation unit 105 is a profile in the depth direction at a predetermined position in the horizontal direction.

The profile is information indicating a relationship between depth directional position and luminance value. The width of the profile in the horizontal direction is one pixel. Original data that can be used to generate the profile is a row of pixels disposed in the depth direction. As described above, the Sobel image is an image having enhanced edges. A luminance value of the Sobel image represents a luminance change in the original image.

The predetermined position where a profile is generated is not limited to a one-dimensional image region. For example, the above-described predetermined position can be a two-dimensional image area that has a width corresponding to several pixels in the horizontal direction and includes pixels disposed in the depth direction.

Alternatively, the above-described predetermined position can be a three-dimensional image area. A layer boundary that is present in the depth direction at a position where the profile is created in the horizontal direction can be identified.

In this case, the horizontal direction is a direction perpendicular to the direction of irradiated signal light (A-scan direction). It is desired that the above-described horizontal direction coincides with the horizontal direction of an image. In almost all of a normal eye, except for the macula and the optic disc, the above-described horizontal direction is a direction along which the layer extends and a direction parallel to the layer.

Further, the above-described depth direction is the direction of irradiated signal light (A-scan direction). It is desired that the depth direction coincides with the vertical direction of an image. In an ordinary display, the above-described A-scan direction is set to be coincident with the vertical direction of a screen.

A retinal layer has a multilayered structure that includes a plurality of layers stacked on top of another in the depth direction. Therefore, in almost all of a normal eye except for the macula and the optic disc, a direction along which two or more layers are sequentially positioned is the depth direction.

The luminance information generation unit 105 generates profiles at predetermined intervals (e.g., at intervals of five pixels) in the horizontal direction. Identification of a layer boundary according to the present invention is not performed at a position other than the position where the profile is created. Any conventional interpolation method can be used to obtain an unidentified layer boundary referring to the position of an already identified layer boundary that has been identified based on the profile.

To detect a layer boundary, the detection unit 106 acquires, based on the profile of a Sobel image at each position, a feature point that indicates the position of each layer boundary of layers that are sequentially positioned in the depth direction.

In the present exemplary embodiment, the detection unit 106 acquires, as the feature point, an edge which is greater than a predetermined threshold value, among edges detectable along the profile in the depth direction.

In the present exemplary embodiment, each edge represents the gradient of a luminance value in an image. The above-described predetermined threshold value is an experimentally determined value and corresponds to a first threshold value according to the present invention.

In the present exemplary embodiment, the layer boundary indicates an interface between two neighboring layers each having a predetermined thickness in a tomography image.

If the resolution of an image is sufficiently high, a layer having a thickness less than one pixel may be detected as a boundary and can be regarded as a boundary.

The first threshold value can be modified and determined for each profile based on a statistic value calculated based on a profile. The detection unit 106 performs the above-described detection processing in the A-scan direction (i.e., in the depth direction) at a plurality of positions of a tomography image in the horizontal direction.

The structure determination unit 1071 can determine a structure according to the number of layer boundaries detected by the detection unit 106. The structure determined by the structure determination unit 1071 represents a layer structure that can be defined by the number of layers or layer boundaries and the position and the type thereof. The structure further includes a pseudo-image or a lesion caused by a blood vessel or a leucoma, in addition to the optic disc, the macula, and other regions.

In the present exemplary embodiment, the structure determination unit 1071 corresponds to a determination unit configured to determine the position and the type of a layer boundary. The structure determination unit 1071 includes a template selection unit 107, a layer boundary identifying unit 108, and a layer boundary interpolation unit 109.

The template selection unit 107 allocates template information to each profile according to the number of feature points each representing the position of a layer boundary acquired from the profile. The template information is information representing the type and the position of each layer boundary as well as a relationship between layer boundaries, i.e., layer areas, in the magnitude of luminance value. The template information represents the type of a plurality of layer boundaries that are sequentially disposed in the depth direction at each of a plurality of positions of a target to be captured in the horizontal direction.

The storage unit 111 stores a plurality of types of templates that are differentiated according to the structure of each retinal layer or considering the presence of a blood vessel. The structure determination unit 1071 identifies the position and the type of a target layer boundary based on the profile with reference to the above-described template information.

The template information is associated with information indicating the number of feature points, when it is stored. Thus, the structure determination unit 1071 can determine an appropriate template based on feature points with reference to the template information.

The template can be created by extracting information indicating the position and the type of a layer boundary and information indicating the relationship between layer boundaries in the magnitude of luminance value from a reference profile that can be created by obtaining an average value or a central value from a plurality of tomography images capturing the same portion of a layer boundary whose position and type have been identified beforehand. The template may include information indicating a luminance value of each layer.

For example, the structure of a retinal layer at the macula or at the optic disc is different from the structure of the retinal layer at other portions. Therefore, the templates prepared in the storage unit 111 include specific templates that correspond to the macula or the optic disc.

Further, if a blood vessel is present at a predetermined position of a retinal layer, signal light is absorbed by the blood vessel. The intensity of the signal light is weakened when it reaches an area beneath the blood vessel. Therefore, the profile may be deformed depending on the presence of a blood vessel.

Therefore, for example, two or more different templates are prepared for the same macula considering the above-described situation (i.e., according to the presence of a blood vessel). It is desired to prepare various types of templates so that at least one template can be applied to any predicable situation (e.g., presence of a lesion).

Experimentally creating template information based on tomography images of numerous eyes to be examined is feasible. Further, to reduce the processing time, it may be useful to limit the number of selectable profiles. The above-described templates are stored in the storage unit 111. Examples of the template are described below in more detail.

The layer boundary identifying unit 108 is functionally operable as an identifying unit or a first identifying unit configured to identify a layer structure in a tomography image by applying a template to each profile.

In the present exemplary embodiment, identification of each layer structure includes identifying the position of the layer structure or the type thereof. The information indicating each identified layer boundary is associated with the profile or the tomography image, and can be stored in the storage unit 111 or in a data server 113. Example of the above-described identifying processing is described below in more detail.

The layer boundary interpolation unit 109 is functionally operable as a setting unit configured to set a search range for a layer boundary portion that has not been identified based on the application of a template. Further, the layer boundary interpolation unit 109 is functionally operable as an identifying unit or a second identifying unit configured to interpolate a layer boundary by identifying the position of an unidentified layer boundary portion.

In the present exemplary embodiment, the layer boundary interpolation unit 109 correlates interpolation completion information with the information indicating the interpolated layer boundary position. Further, the layer boundary interpolation unit 109 stores the information indicating the interpolated layer boundary position in association with the profile or the tomography image in the storage unit 111 or in the data server 113.

An example of the above-described interpolation processing is described below in detail with reference to a flowchart illustrated in FIG. 11.

The display control unit 110 can control a display unit 112 to display a tomography image together with information indicating the type and position of each layer boundary. In the above-described control, the display control unit 110 causes the display unit 112 to use a unique color for each layer boundary included in the tomography image according to the type of each layer.

Further, it is useful that the display control unit 110 controls the display unit 112 to differentiate a display pattern for the position of a layer boundary identified based on template information from a display pattern for the position of a layer boundary identified by interpolation processing.

The storage unit 111 stores information to be required by respective blocks of the image processing apparatus 101 and information output from respective blocks. For example, the detection unit 106 can use the first threshold value or its calculation method stored in the storage unit 111. The template selection unit 107 can use template information stored in the storage unit 111. The layer boundary interpolation unit 109 can use a search range setting value and a second threshold value stored in the storage unit 111.

The display unit 112 is, for example, a liquid crystal display device, which can display a tomography image output by the image processing apparatus 101 together with the position and the type of each layer boundary.

The data server 113 is functionally operable as a storage unit configured to store tomography images acquired by the tomography image acquisition apparatus 102 together with bibliographic information.

Figure 2:
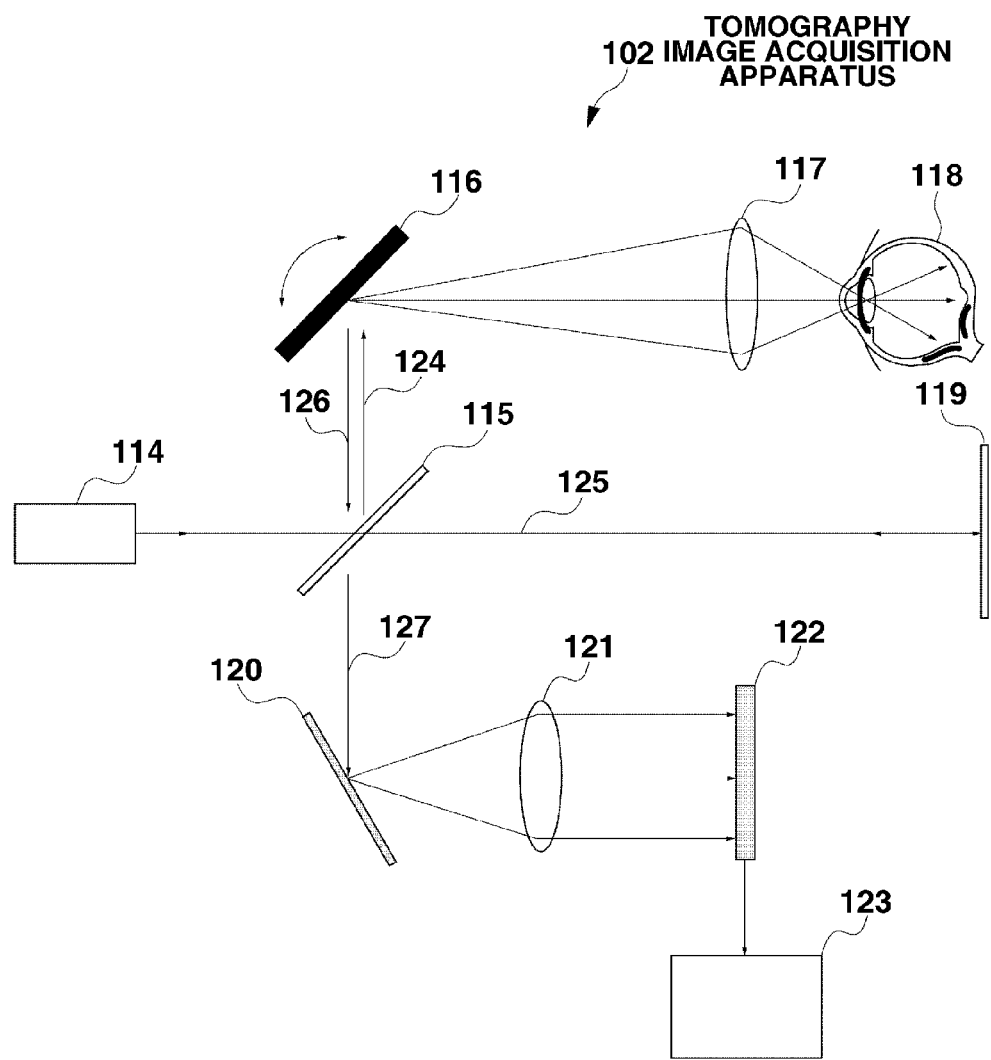
FIG. 2 illustrates an example configuration of a tomography image acquisition apparatus according to the first exemplary embodiment of the present invention.

An example configuration of the tomography image acquisition apparatus 102 is described below in more detail with reference to FIG. 2. The tomography image acquisition apparatus 102 is a so-called Fourier-Domain type optical coherence tomography imaging apparatus. The tomography image acquisition apparatus 102 can capture an image of an eye to be examined (not illustrated) in response to an instruction of an operator (not illustrated). The tomography image acquisition apparatus 102 can transmit a captured image to the image processing apparatus 101 and to the data server 113.

A light source 114 emits light. A beam splitter 115 is capable of dividing the light emitted from the light source 114 into measurement light 124 and reference light 125. The measurement light 124 reaches an eye 118 (i.e., a target to be observed) and returns as feedback light 126. The feedback light 126 (i.e., the light returning from the eye 118) includes reflection light and scattered light of the measurement light.

Further, the beam splitter 115 is functionally operable as a coherent light generation unit configured to multiplex the feedback light 126 and the reference light 125 to generate coherent light 127. A diffraction grating 120 disperses the coherent light 127. The dispersed coherent light passes through a lens 121 and forms an image on a one-dimensional sensor 122.

The one-dimensional sensor 122 includes a plurality of pixel circuits each outputting an electric signal that represents the quantity of received light. An image formation unit 123 performs Fourier transformation with reference to an internal position of the one-dimensional sensor 122 (i.e., the number of waves of the coherent light), and obtains a tomography image of the eye 118.

The light source 114 is described below in more detail. The light source 114 is a super luminescent diode (SLD), which is known as a representative low coherent light source. The light emitted from the light source 114 has a wavelength of 830 nm. The light emitted from the light source 114 has a bandwidth of 50 nm.

The bandwidth of the light emitted from the light source 114 is an important parameter because the bandwidth significantly influences the resolution of an obtained tomography image in the optical axis direction. Further, the type of the light source 114 is not limited to the above-described SLD. Any other type of light source can be used as the light source 114, if it can emit low coherent light. For example, amplified spontaneous emission (ASE) can be used as the light source 114.

Further, near infrared light is usable as the light to be emitted from the light source 114 because the near infrared light has a wavelength effective to measure an eye. Further, the wavelength significantly influences the resolution of an obtained tomography image in the horizontal direction. Therefore, it is desired to set the wavelength as short as possible. In the present exemplary embodiment, the selected wavelength is 830 nm. Another wavelength may be selected depending on the portion of an observation target to be measured.

An optical path of the reference light 125 is described below. The reference light 125 (i.e., one light component separated (dispersed) by the beam splitter 115) is reflected by a mirror 119 (i.e., a reference object) and returns to the beam splitter 115. When the length of the optical path of the reference light 125 is equal to the length of an optical path of the measurement light 124, the reference light 125 can interfere with the measurement light 124.

Next, the optical path of the measurement light 124 is described. The measurement light 124 (i.e., the other light component separated (dispersed) by the beam splitter 115) reaches a mirror of an XY scanner 116, which can change the direction of the measurement light 124 toward the eye 118. The XY scanner 116 is functionally operable as a scanning optical system that performs two-dimensional raster scanning on a retina of the eye 118 in a direction perpendicular to the optical axis by successively changing the direction of the measurement light 124.

Although not illustrated in the drawing, the XY scanner 116 is composed of two mirrors (i.e., an X-scanning mirror and a Y-scanning mirror) that are positioned adjacent to each other. Further, the measurement light 124 and the XY scanner 116 are adjusted beforehand so as to satisfy the positional relationship that the center of the measurement light 124 coincides with the rotational center of the mirror of the XY scanner 116.

The measurement light 124, after passing through a lens 117, is converged onto the retina. When the measurement light 124 reaches the eye 118 through the above-described optical system, the measurement light 124 becomes the feedback light 126 when reflected and scattered by the retina of the eye 118.

In the present exemplary embodiment, generating a one-dimensional image with the measurement light 124 reaching a point on the retina is referred to as "A-scan" processing and the generated one-dimensional image is referred to as "A-scan image." Further, generating a two-dimensional image by performing the A-scan processing at predetermined intervals along a predetermined line on the retinal surface is referred to as "B-scan" processing and the generated two-dimensional image is referred to as "B-scan image."

A plurality of A-scan images can be obtained at a plurality of positions when the B-scan is performed at predetermined intervals by successively changing the incidence position of the measurement light. A two-dimensional B-scan image can be obtained by performing interpolation processing on the obtained plurality of A-scan images.

Further, an ordinary OCT apparatus includes a scanning-type laser ophthalmoscope (not illustrated) capable of monitoring an image-capturing position or an optical system capable of capturing a two-dimensional image of an ocular fundus.

Next, an example spectroscopic system is described. As described above, the coherent light 127 is separated (dispersed) by the diffraction grating 120. The above-described dispersion is performed under the same wavelength conditions as the central wavelength and the bandwidth of the light source. Further, the one-dimensional sensor to be used to measure the coherent light is generally a charge-coupled device (CCD) type sensor or a complementary metal oxide semiconductor (CMOS) type sensor.

The image processing apparatus 101 analyzes a tomography image captured by the above-described tomography image acquisition apparatus 102 (i.e., the optical coherence tomography imaging apparatus). In the present exemplary embodiment, the tomography image acquisition apparatus 102 may not be the optical coherence tomography imaging apparatus itself and may be functionally operable as an apparatus that can acquire a tomography image from the data server 113 if the data server 113 stores tomography images captured by the optical coherence tomography imaging apparatus.

Next, an example of the tomography image of retinal layers that can be acquired by the above-described tomography image acquisition apparatus 102 is described below with reference to FIGS. 3A and 3B. The tomography image illustrated in FIG. 3 has a layer structure that can be identified by the image processing apparatus 101.

Figure 3A:
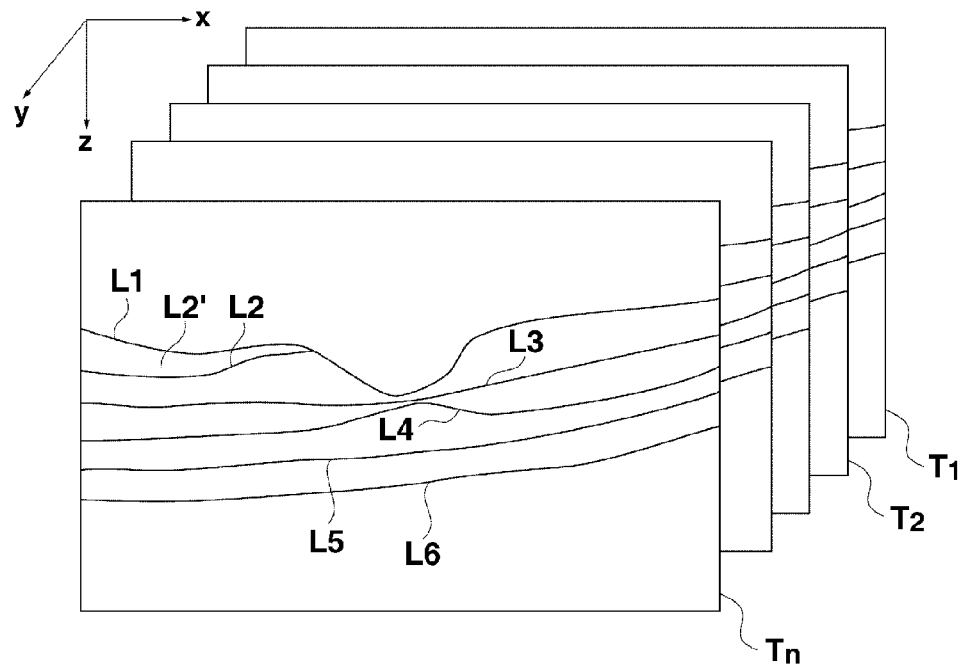
FIG. 3A schematically illustrates an example tomography image of retinal layers captured in a region including a macula.
Figure 3B:
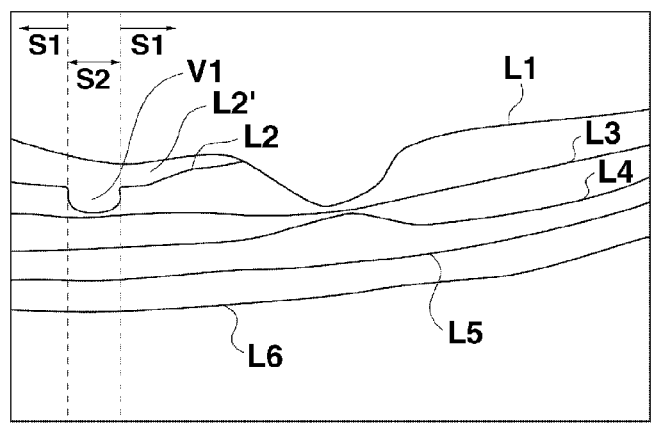
FIG. 3B schematically illustrates another example tomography image of retinal layers captured in a region including a macula and a blood vessel positioned adjacent to each other.

FIGS. 3A and 3B illustrate examples of the structure of retinal layers. The layer structure identification processing according to the present exemplary embodiment can be applied to the retinal layers illustrated in FIGS. 3A and 3B.

FIG. 3A schematically illustrates an example tomography image of retinal layers captured in a region including the macula, in which each solid line represents a layer boundary. Each of a plurality of two-dimensional tomography images (B-scan images, hereinafter referred to as "tomography images") T1 to Tn, each including a macula image, can be obtained by performing the A-Scan processing along a line on the retinal surface so as to obtain a two-dimensional image.

The above-described A-scan processing is discretely (i.e., discontinuously) performed at predetermined intervals along a line. An appropriate interpolation method can be employed to obtain an interpolated two-dimensional image that corresponds to an intermediate point between two neighboring discrete points where the A-scan processing has been performed.

The tomography image Tn includes an interface L1 of an inner limiting membrane (ILM), a nerve fiber layer (NFL) L2', and a boundary L2 between the nerve fiber layer L2' and an underlying layer thereof. Further, the tomography image Tn includes a boundary L3 between an inner plexiform layer and an underlying layer thereof and a boundary L4 between an outer plexiform layer and an underlying layer thereof. Further, the tomography image Tn includes a boundary L5 of an interface between inner and outer segments of the photoreceptors (IS/OS) and a lower boundary L6 of a retinal pigment epithelium (RPE). As described above, the retina has a layer structure that is composed of a plurality of layers that are sequentially positioned in the depth direction.

Discriminating the boundary between the IS/OS and the RPE may be difficult if the performance of the OCT imaging apparatus is insufficient, although the above-described detection accuracy is sufficient enough to realize the present invention.

Further, the inner limiting membrane (ILM) is a thin layer, although it has a predetermined thickness. Similarly, the interface between inner and outer segments of the photoreceptors (IS/OS) is a thin layer. Therefore, these layers are recognized as lines when an image is displayed.

Therefore, in a case where a low-resolution image is processed, discriminating the interface of the inner limiting membrane from the inner limiting membrane itself may be difficult. In this case, identifying the interface of the inner limiting membrane is not different from identifying the inner limiting membrane itself. Further, the layer boundary is substantially identical to the interface.

In general, the retina has a layer structure that is composed of a plurality of retinal layers as described above. However, the retinal layer structure may be different or modified if the position to be examined is changed or if a lesion is present.

FIG. 3B schematically illustrates another tomography image of retinal layers in a region including the macula. The tomography image illustrated in FIG. 3B includes a blood vessel V1. In this case, red blood cells contained in the blood vessel attenuate the signal light. Therefore, in a horizontal area S2 in which the blood vessel V1 is present, a pseudo-image may be generated because it is difficult to capture an image of an underlying area positioned beneath the blood vessel V1.

Accordingly, an apparent structure that can be identified based on the tomography image in the area S2 may be different from that obtainable from an image of an area S1 in which no blood vessel is present. Similarly, if a leucoma is present, a pseudo-image may be generated because it is difficult to capture an image of an underlying area positioned beneath the leucoma.

The region where the above-described lesion or similar abnormality appears, i.e., the region where the structure changes greatly, is a vertical layer zone extending from the inner limiting membrane L1 to boundary L6 of the retinal pigment epithelium. Therefore, after identifying the above-described layers, their inner layers are identified.

Figure 4:
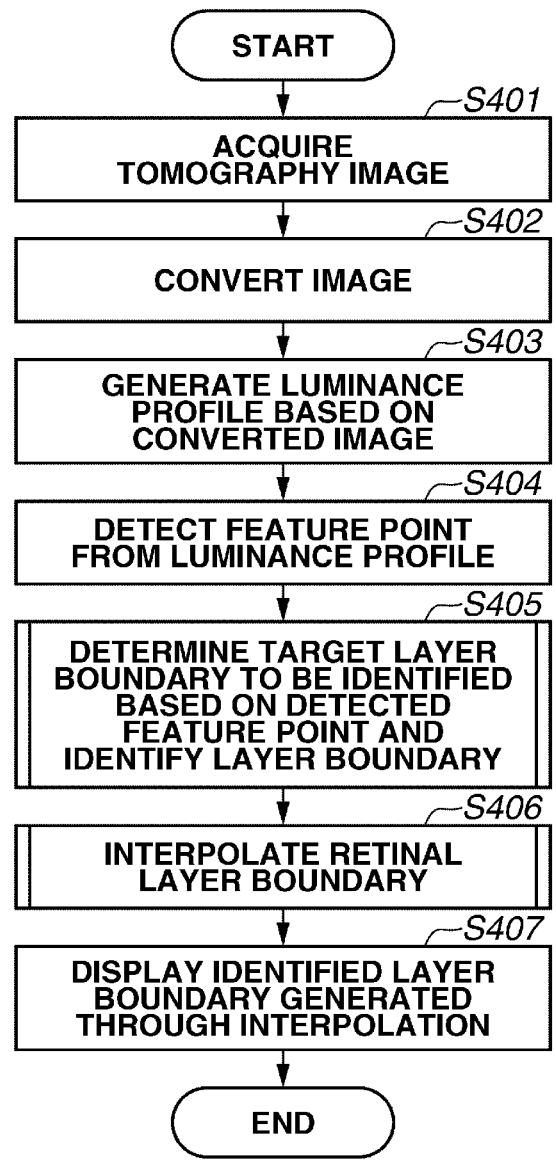
FIG. 4 is a flowchart illustrating an example flow of processing that can be performed by an image processing apparatus according to the first exemplary embodiment of the present invention.

An example flow of processing that can be performed by the image processing apparatus 101 having the above-described configuration is described below with reference to a flowchart illustrated in FIG. 4. The processing according to the present exemplary embodiment is identifying the interface of the inner limiting membrane L1 and the interface between inner and outer segments of the photoreceptors (IS/OS).

The inner limiting membrane L1 or the interface between inner and outer segments of the photoreceptors (IS/OS) includes a boundary between another layer and the layer itself.

In the present exemplary embodiment, processing is performed to identify the position of an interface positioned on the upper side when seen in the depth direction because an edge from the lower side to the upper side is seen.

If the resolution of an image is insufficient, the width of the above-described layer may be narrower than one pixel of the image. In this case, it may be difficult to determine whether the position identified as a layer boundary represents an upper-side interface, a lower side interface, or the layer itself. In such a case, identifying an interface of a layer is not different from identifying the layer itself.

(Step S401) In step S401, the image acquisition unit 103 acquires an OCT image from the tomography image acquisition apparatus 102.

(Step S402) In step S402, the image conversion unit 104 performs image conversion processing on the OCT image acquired by the image acquisition unit 103.

In the present exemplary embodiment, the image conversion unit 104 applies the median filter and two types of Sobel filters to the acquired tomography image. As described above, an image obtained through the above-described conversion processing is referred to as a median image when the median filter is used.

One of the above-described two types of Sobel filters is a Sobel filter that can enhance an edge from a low-luminance pixel to a high-luminance pixel in the depth direction of the A-scan line. The other of the above-described two types of Sobel filters is a Sobel filter that can enhance an edge from a high-luminance pixel to a low-luminance pixel. Hereinafter, when converted images are obtained through the above-described conversion processing using the Sobel filters, the obtained images are sequentially referred to as Sobel image A and Sobel image B.

Figure 5A:
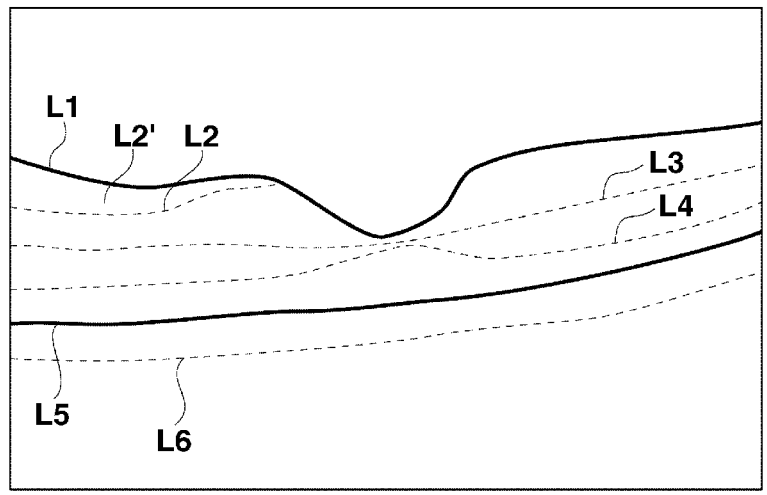
FIG. 5A illustrates an example of a converted image that can be generated by an image conversion unit according to the first exemplary embodiment of the present invention.

FIG. 5A illustrates an example of the Sobel image A, which can be obtained by applying one of the above-described two types of Sobel filters to an OCT image. The Sobel image A illustrated in FIG. 5A includes enhanced edges of the inner limiting membrane and the interface between inner and outer segments of the photoreceptors.

Figure 5B:
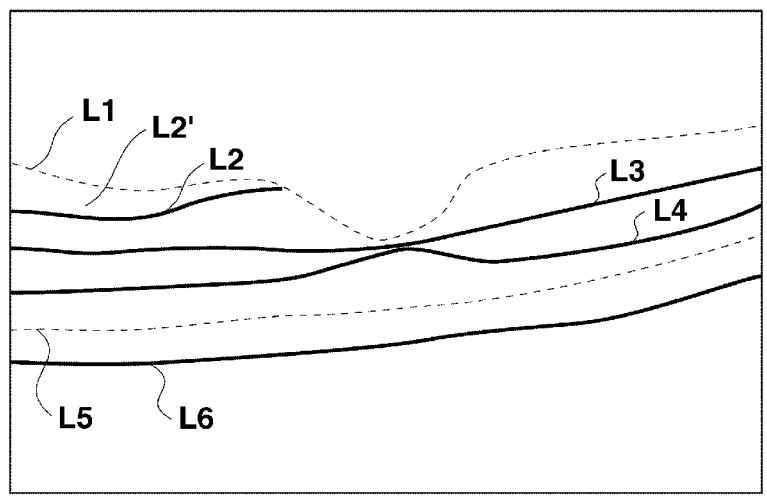
FIG. 5B illustrates an example of a converted image that can be generated by an image conversion unit according to the first exemplary embodiment of the present invention.

FIG. 5B illustrates an example of the Sobel image B, which can be obtained by applying the other of the above-described two types of Sobel filters to the same OCT image. The Sobel image B illustrated in FIG. 5B includes enhanced edges of the nerve fiber layer boundary, the inner plexiform layer, the outer plexiform layer, and the retinal pigment epithelium.

The median image, the Sobel image A, and the Sobel image B obtained through the image conversion processing in the step S402 are stored in the data server 113.

The image conversion method is not limited to the above-described method. For example, the above-described median filter can be replaced by a smoothing filter (e.g., an average value filter). Further, the image conversion processing according to the present exemplary embodiment can be realized by using a gradation conversion filter (capable of performing gamma correction) or a morphology filter instead of using the smoothing filter or an edge enhancement filter.

Alternatively, a luminance value of the original image can be directly used as an input for the next step when the above-described image conversion processing is skipped.

(Step S403) In step S403, the luminance information generation unit 105 generates luminance information based on the converted image obtained in step S402.

In the present exemplary embodiment, the luminance information generation unit 105 checks the luminance value in the depth direction, on a pixel by pixel basis, in an image area positioned at a predetermined position. Further, the luminance information generation unit 105 generates a profile that represents the obtained luminance information.

The above-described predetermined position is a one-dimensional image region extending along the A-scan line, i.e., in the depth direction.

The A-scan line indicates a row of pixels disposed in the depth direction of the image. The depth direction of a profile image coincides with the direction of the axial scanning (A-scan processing) performed on an OCT image. However, the row of pixels may not be a row of pixels that corresponds to the position where the A-scan processing has been performed.

In the present exemplary embodiment, the A-scan line scanning processing is performed at intervals of five pixels on a tomography image having a width of 256 pixels and a height of 250 pixels. Therefore, fifty A-scan lines are set for a piece of B-scan image. Each of the fifty A-scan lines is designated as a target to be identified with respect to the retinal layer boundary.

The luminance information generation unit 105 generates a profile along each of the above-described A-scan lines. The above-described processing is performed on each converted image obtained in the previous step and the obtained data is stored in the data server 113 (or may be stored in the storage unit 111).

However, the luminance information generation method is not limited to the above-described method that is characterized in that generation of the luminance information is performed on a pixel by pixel basis. For example, the luminance information can be generated based on a block area composed of a plurality of pixels. Further, the scanning processing along the A-scan line may be performed at different intervals.

(Step S404) In step S404, the detection unit 106 acquires a feature area based on the luminance information created in step S403.

In the present exemplary embodiment, the detection unit 106 checks the profile generated based on the Sobel image A. Then, the detection unit 106 acquires an area whose luminance is equal to or greater than a predetermined threshold value as the feature area. The Sobel image is an image including an enhanced edge. The area to be detected by the detection unit 106 is an area in which the luminance change in the depth direction is equal to or greater than a predetermined threshold value. Hereinafter, the area acquired by the detection unit 106 is referred to as a peak area or a peak.

Figure 6:
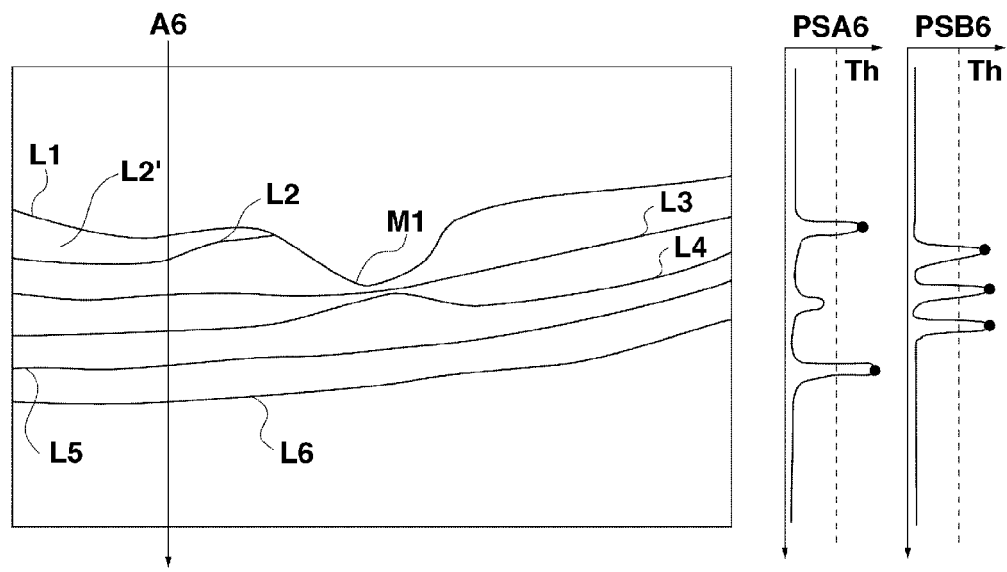
FIG. 6 illustrates an example of profiles that can be generated by a luminance information generation unit according to the first exemplary embodiment of the present invention.

Example processing to be performed to detect a peak from a tomography image is described below with reference to FIG. 6. In the OCT image illustrated in FIG. 6, a vertical line A6 represents one of the A-scan lines (i.e., a row of pixels). The OCT image illustrated in FIG. 6 further includes a profile PSA6 of the Sobel image A taken along the A-scan line A6 and a profile PSB6 of the Sobel image B taken along the A-scan line A6.

As described in step S302, the profile of the Sobel image A and the profile of the Sobel image are characterized in that a specific retinal layer boundary is enhanced and the enhanced boundary appears as a peak in the graph representing a change in the luminance.

In the present exemplary embodiment, a threshold Th is set and an area whose luminance value is equal to or greater than the threshold Th is regarded as a peak.

The above-described threshold value corresponds to the predetermined threshold value or the first threshold value according to the present invention. As described above, the peak detection processing is performed along each A-scan line. Peak information (e.g., position and magnitude) obtained through the above-described processing is stored in the data server 113.

In the present exemplary embodiment, the position of the peak represents the position of a local maximum point in a detected peak area and the magnitude of the peak represents the magnitude of the local maximum point. The local maximum point in the peak area is regarded as a feature point.

In the present exemplary embodiment, the detection unit 106 acquires the above-described peak position as the position of a layer boundary, although the type of a layer boundary whose position has been identified is not yet identified at this moment.

The feature area detection method is not limited to the above-described method. For example, any other point (e.g., a profile maximum point or a profile minimum point) in the feature area can be used to detect the feature point.

In steps S405 and S406, the structure determination unit 1071 performs processing to determine a structure based on the layer boundary or the edge detected by the detection unit 106. In the present exemplary embodiment, the structure determination unit 1071 determines the type of a layer boundary that is present in each of the A-scan lines.

(Step S405) In step S405, the template selection unit 107 roughly estimates the structure of a retinal layer to be identified based on the feature points detected in step S404. Then, the template selection unit 107 selects an appropriate template that is similar to the detected layer structure.

Through the above-described processing, a layer boundary type that corresponds to any one of layer boundaries at the peak position acquired by the detection unit 106 can be determined. Then, the layer boundary identifying unit 108 identifies a correspondence relationship in relation to the type of the detected layer boundary based on the position acquired in step S404 and the template information.

Figure 7:
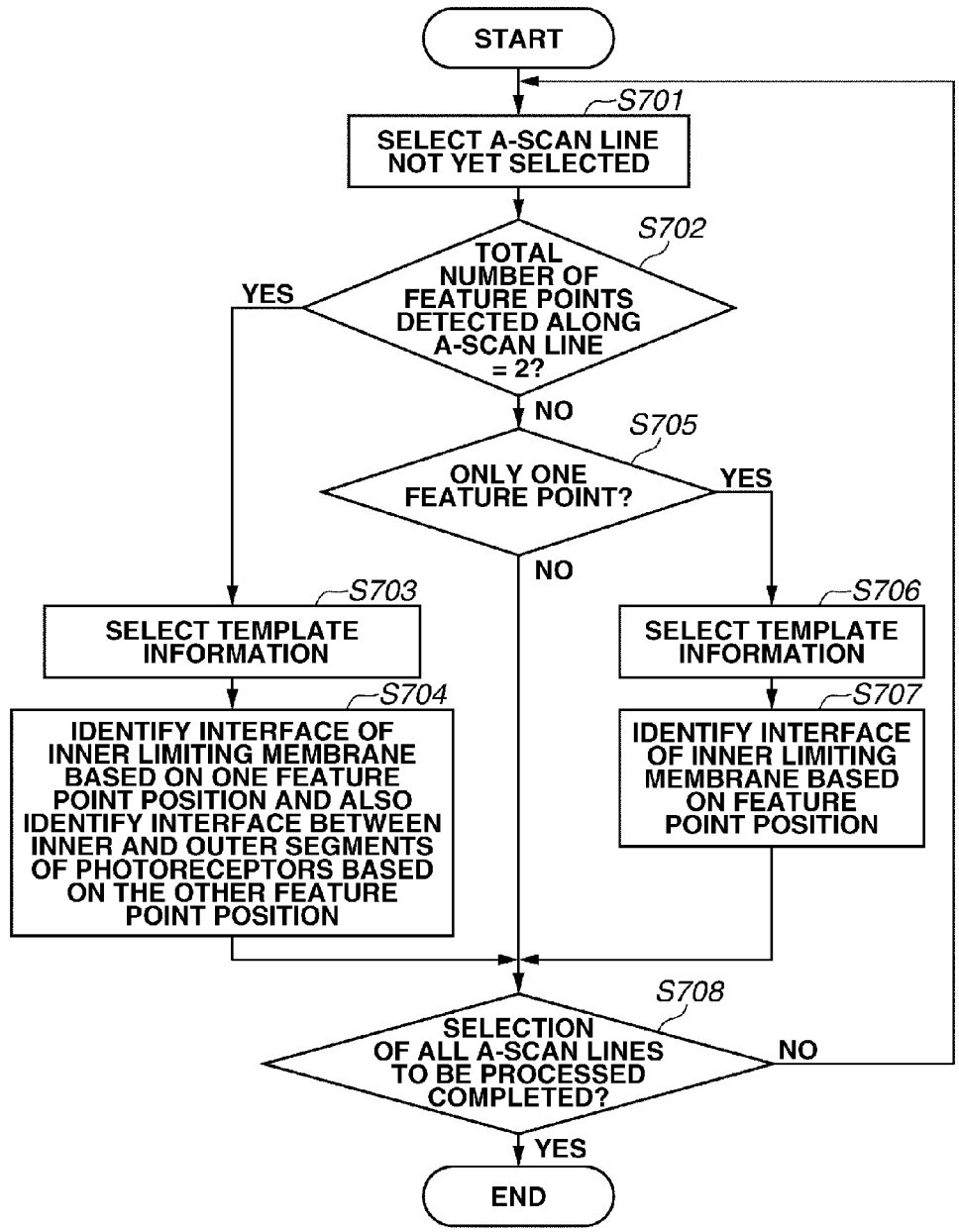
FIG. 7 is a flowchart illustrating an example flow of processing that can be performed by a template selection unit and a layer boundary identifying unit according to the first exemplary embodiment of the present invention.

Detailed processing to be performed in step S405 is described below with reference to the flowchart illustrated in FIG. 7. The flowchart illustrated in FIG. 7 describes processing to be performed for each A-scan line. If the processing according to the flowchart illustrated in FIG. 7 is thoroughly completed for all of the A-scan lines, the processing proceeds to step S406.

(Step S406) In step S406, the layer boundary interpolation unit 109 interpolates the retinal layer boundary along each A-scan line from which no retinal layer boundary was identified. Detailed processing to be performed in step S406 is described below with reference to the flowchart illustrated in FIG. 11.

Figure 11:
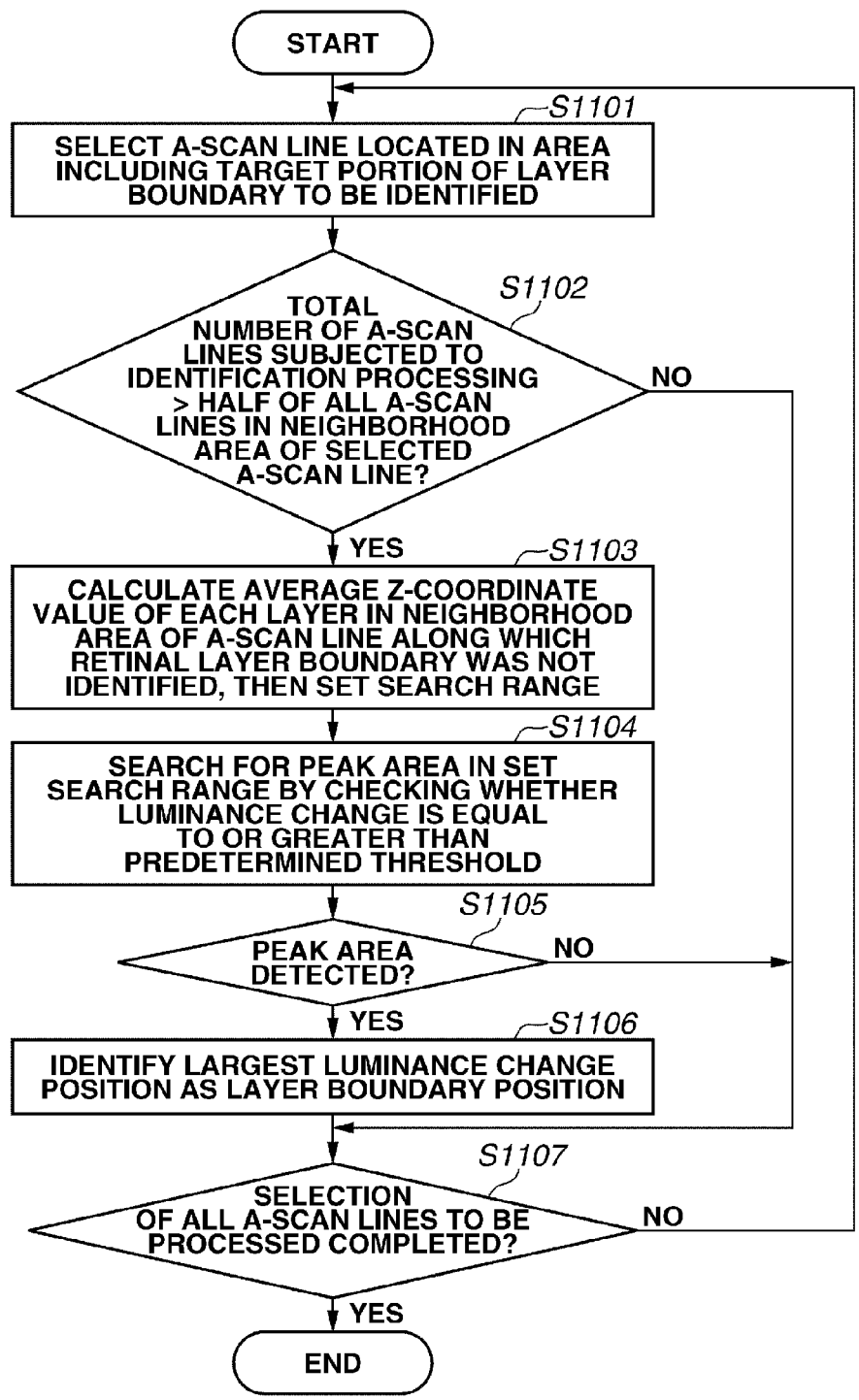
FIG. 11 is a flowchart illustrating an example flow of processing that can be performed by a layer boundary interpolation unit according to the first exemplary embodiment of the present invention.

In the flowchart illustrated in FIG. 11, the layer boundary interpolation unit 109 performs branched processing for each of the A-scan lines. If the processing according to the flowchart illustrated in FIG. 11 is thoroughly completed for all of the A-scan lines, the processing proceeds to step S407.

(Step S407) In step S407, the display control unit 110 causes the display unit 112 to display interpolated lines that can be obtained by connecting boundary points of the inner limiting membrane or the interface between inner and outer segments of the photoreceptors, which have been identified at predetermined intervals along each A-scan line.

As described above, when the type of each layer boundary to be identified is determined with reference to the features than can be extracted from an image, it becomes feasible to eliminate errors in identifying the type of each layer boundary.

Further, when a template is selected and applied in the above-described processing to identify each layer boundary, the position of the layer boundary can be identified with reference to the features extracted from an image. Therefore, the position of each detected layer boundary can be identified accurately or reliably.

Next, an example flow of the processing to be performed in step S405, i.e., example processing that can be performed by the template selection unit 107 and the layer boundary identifying unit 108, is described below with reference to FIG. 7.

(Step S701) In step S701, the template selection unit 107 selects a row of pixels (A-scan line) as a target to be analyzed. More specifically, the template selection unit 107 successively selects a row of pixels disposed in the depth direction at intervals of five pixels in the horizontal direction. The interval in the above-described processing is not limited to five pixels and can be arbitrarily set.

(Step S702) In step S702, the template selection unit 107 counts the total number of the feature points along each A-scan line and determines the type of each detected layer boundary (i.e., a target to be identified). If the total number of the feature points is two, the template selection unit 107 determines that each of the interface of the inner limiting membrane and the interface between inner and outer segments of the photoreceptors as a layer boundary to be identified. Then, the processing proceeds to step S703. If the total number of the feature points is not two, the processing proceeds to step S705.

Figure 8:
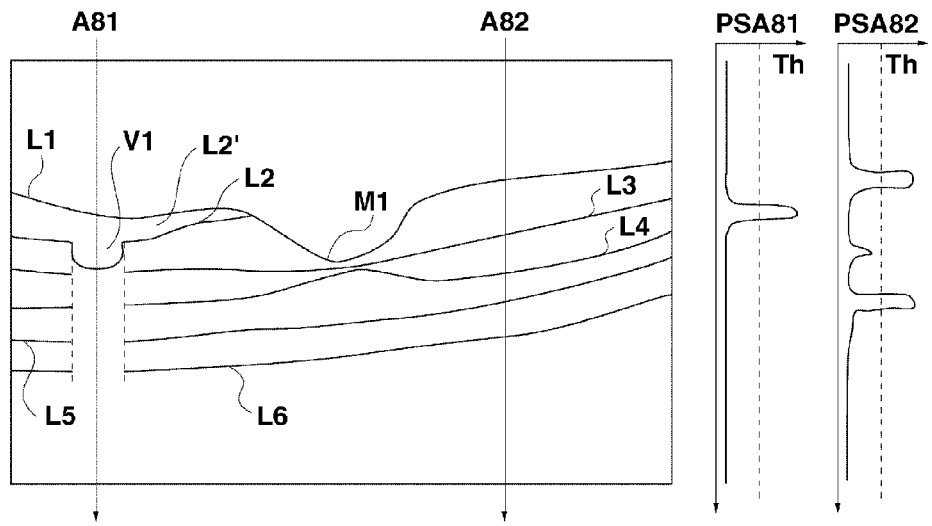
FIG. 8 schematically illustrates example processing that can be performed by the template selection unit according to the first exemplary embodiment of the present invention.

Detailed processing is described below with reference to FIG. 8. FIG. 8 illustrates an example tomography image of retinal layers, in which vertical lines A81 and A82 represent two A-scan lines. Further, PSA81 and PSA81 represent profiles obtained from the Sobel image A.

To estimate a retinal layer, the template selection unit 107 counts the number of peaks appearing on each profile. The tomography image illustrated in FIG. 8 includes the blood vessel V1 that generates a pseudo-image. Due to the presence of the blood vessel V1, the interface between inner and outer segments of the photoreceptors cannot be identified along or in the vicinity of the A-scan line A81 in the tomography image illustrated in FIG. 8.

Therefore, the template selection unit 107 counts the number of peaks appearing on the profile of the Sobel image A along each A-scan line. If the total number of the counted peaks is two, the template selection unit 107 determines that the inner limiting membrane and the interface between inner and outer segments of the photoreceptors may be present in the image when taken along or in the vicinity of the A-scan line.

In this case, the template selection unit 107 determines that the type of the target (i.e., the layer boundary) to be identified is both the inner limiting membrane and the interface between inner and outer segments of the photoreceptors. Subsequently, the processing proceeds to step S702.

If only one peak is present, the template selection unit 107 determines that only the inner limiting membrane may be present in the image when taken along or in the vicinity of the A-scan line. In this case, the template selection unit 107 determines that the type of the target (i.e., the layer boundary) to be identified is the inner limiting membrane. Subsequently, the processing proceeds to step S303.

If the total number of the counted peaks is not the above-described number (two or one), the template selection unit 107 determines that a noise may be present. In this case, the template selection unit 107 determines that the type of the target (i.e., the layer boundary) to be identified is nothing. The template selection unit 107 does not identify any retinal layer boundary along the A-scan line.

As described above, even when a layer boundary is detected based on an edge or edges by the detection unit 106, if an appropriate template is not present, the template selection unit 107 determines that an anatomical layer boundary type cannot be identified and does not perform layer boundary identification processing because the detected layer boundary is regarded as a noise.

(Step S703) In step S703, the template selection unit 107 selects a template from the storage unit 111 according to the number of layer boundaries detected based on feature points (i.e., edges).

(Step S704) The layer boundary identifying unit 108 performs layer boundary identification processing along the A-scan line that was presumed in step S702 as positioning in an area where both the interface of the inner limiting membrane and the interface between inner and outer segments of the photoreceptors are present.

In the present exemplary embodiment, the layer boundary identifying unit 108 successively identifies, from a shallow side, the positions of two feature points as the interface of the inner limiting membrane and the interface between inner and outer segments of the photoreceptors with reference to the template information.

Figure 9:
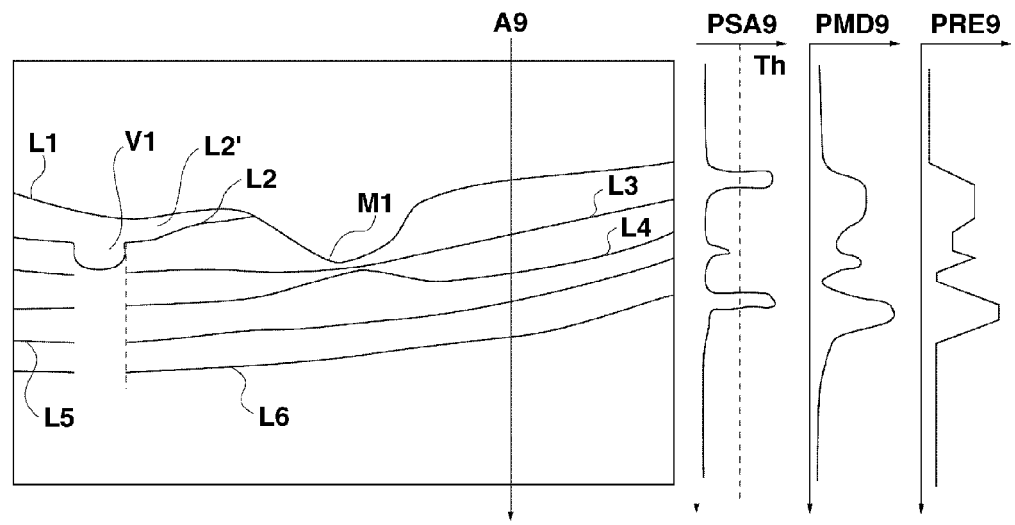
FIG. 9 schematically illustrates example processing that can be performed by the layer boundary identifying unit according to the first exemplary embodiment of the present invention.

The layer boundary identifying unit 108 can also perform the following processing. Example processing that can be performed by the layer boundary identifying unit 108 is described below in detail with reference to FIG. 9. FIG. 9 illustrates an example tomography image of retinal layers, in which a vertical line A9 represents one of the A-scan lines. The tomography image illustrated in FIG. 9 further includes a profile PSA9 obtained from the Sobel image A and a profile PMD9 obtained from the median image.

Further, a plurality of profiles used in the present step includes a reference profile PRE9 that can be derived from the profile obtained from the median image. The reference profile PRE9 is additionally prepared to identify the boundaries of the target two layers (i.e., the interface of the inner limiting membrane and the interface between inner and outer segments of the photoreceptors). The reference profile PRE9 is a typical example of the profile taken along the A-scan line extending in an area where both of the target two layers (i.e., the interface of the inner limiting membrane and the interface between inner and outer segments of the photoreceptors) are present.

In the present exemplary embodiment, the typical example indicates a tendency of the luminance between respective layers along the A-scan line extending in an area where both of the target two layers (i.e., the interface of the inner limiting membrane and the interface between inner and outer segments of the photoreceptors) are present, in which no noise is present.

For example, when the luminance value is observed in an intermediate region between the interface of the inner limiting membrane and the interface between inner and outer segments of the photoreceptors, there is a tendency that the luminance value becomes higher in a region adjacent to the inner limiting membrane because of the presence of the nerve fiber layer and the inner plexiform layer. The reference profile PRE9 to be prepared in the present exemplary embodiment possesses the above-described tendency in the luminance features.

The reference profile PRE9 is not limited to the above-described example. Any other profile can be employed if the luminance tendency of each retinal layer and a positional relationship between retinal layers can be identified based on the employed profile.

The reference profile PRE9 does not reflect the thickness of each retinal layer, although the thickness is generally variable depending on the position of the A-scan line. Therefore, the reference profile PRE9 is employable for any A-scan line extending in an area where both of the target two layers (i.e., the interface of the inner limiting membrane and the interface between inner and outer segments of the photoreceptors) are present.

The layer boundary identifying unit 108 uses the reference profile PRE9 to determine whether the detected two peaks coincide with the above-described two layers (i.e., the interface of the inner limiting membrane and the interface between inner and outer segments of the photoreceptors)

First, the layer boundary identifying unit 108 calculates an average luminance value between respective peaks appearing on the profile PSA9. The layer boundary identifying unit 108 uses, as a luminance value, a value of the profile PMD9 corresponding to the position of the profile PSA9.

The layer boundary identifying unit 108 refers to two peaks of the profile PSA9 as a first peak and a second peak, respectively, which are positioned in this order from the shallow side. The layer boundary identifying unit 108 calculates the average luminance value in a range extending from the first peak to the second peak (hereinafter, referred to as "peak-to-peak A1"). The range "peak-to-peak A1" includes two equally divided ranges. One of the above-described two divided ranges, which is adjacent to the first peak, is referred to as "peak-to-peak A11." The other of the above-described two divided ranges, which is adjacent to the second peak, is referred to as "peak-to-peak A12."

Further, the layer boundary identifying unit 108 calculates an average luminance value of the background (i.e., the remaining area other than the retinal layers) of the image. In the present exemplary embodiment, the layer boundary identifying unit 108 performs binarization processing using a threshold value that can be experimentally determined for the median image.

The above-described average luminance value calculation by the layer boundary identifying unit 108 is exclusively performed for a target area whose luminance value is less than the threshold value. The background average luminance value calculation method is not limited to the above-described method.

The threshold value to be used in the binarization processing can be determined according to the discriminant analysis method or the Percentile method (P-tile method). Further, it may be useful that the layer boundary identifying unit 108 calculates an average luminance value using luminance values at an upper edge and a lower edge of an image that does not include any retinal layers.

Next, the layer boundary identifying unit 108 compares the calculated average luminance values to determine a relationship between them in the magnitude while taking the reference profile PRE9 into consideration. Two conditions to be satisfied with respect to the average luminance values, which can be derived from the reference profile PRE9, are peak-to-peak A1>background average luminance value and peak-to-peak A11>peak-to-peak A12.

The layer boundary identifying unit 108 confirms whether the calculated average luminance values coincide with the above-described two layers (i.e., the interface of the inner limiting membrane and the interface between inner and outer segments of the photoreceptors) by checking whether the calculated average luminance values satisfy the above-described conditions.

If the above-described conditions are all satisfied, the layer boundary identifying unit 108 identifies the first peak as the interface of the inner limiting membrane and identifies the second peak as the interface between inner and outer segments of the photoreceptors. The identified relationship is stored in the data server 113.

If any one of the above-described conditions is not satisfied, the layer boundary identifying unit 108 determines that there is not any template that suits for the concerned A-scan line and does not identify any retinal layer boundary.

(Step S705) In step S705, the template selection unit 107 determines whether the total number of the edges counted along the A-scan line is only one. If there is only one counted edge, the template selection unit 107 identifies the interface of the inner limiting membrane as a layer boundary to be identified. Then, the processing proceeds to step S706.

If there is not any counted edge or if the total number of the counted edges is three or more, the template selection unit 107 determines that an appropriate template is not present. Then, the processing proceeds to step S708.

As described above, if there is not any appropriate template that can be applied to a detected layer boundary, the template selection unit 107 presumes that the layer boundary detection has failed and does not perform identification processing.

As described above, the template selection unit 107 performs layer structure determination processing along the A-scan line using the entire information of the A-scan line. Therefore, the layer structure determination according to the present exemplary embodiment is robust against noise and structural change (or modification).

(Step S706) In step S706, the template selection unit 107 selects a template that is applicable when only one feature point is present, and acquires the selected template from the storage unit 111.

(Step S707) The layer boundary identifying unit 108 performs layer boundary identification processing along the A-scan line that was determined as positioning in an area where only the inner limiting membrane is present in an image.

In this case, the layer boundary identifying unit 108 identifies the position of one feature point as the interface of the inner limiting membrane with reference to the template information.

Figure 10:
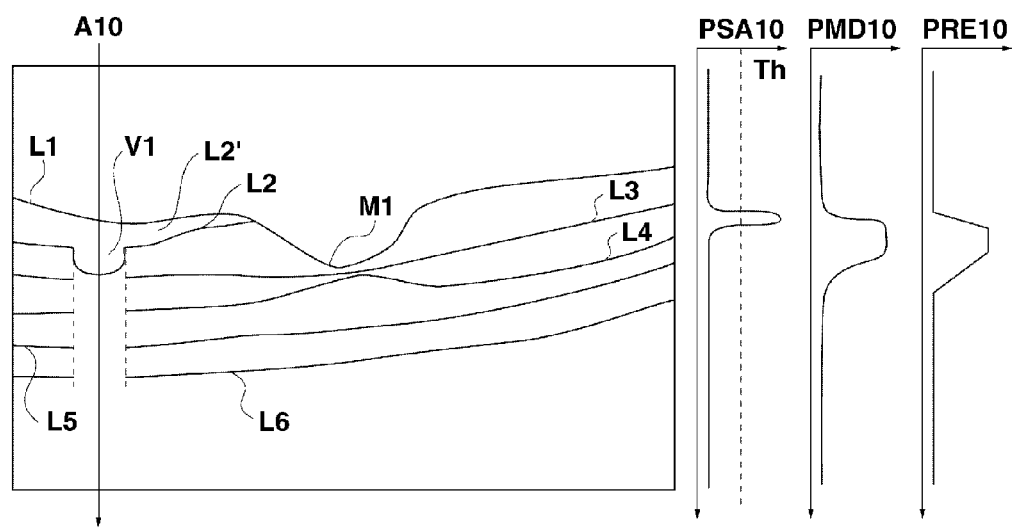
FIG. 10 schematically illustrates example processing that can be performed by the layer boundary identifying unit according to the first exemplary embodiment of the present invention.

The layer boundary identifying unit 108 can also perform the following processing. Example processing that can be performed by the layer boundary identifying unit 108 is described below in detail with reference to FIG. 10. FIG. 10 illustrates an example tomography image of retinal layers, in which a vertical line A10 represents one of the A-scan lines. The tomography image illustrated in FIG. 10 further includes a profile PSA10 obtained from the Sobel image A and a profile PMD10 obtained from the median image.

Further, a plurality of profiles used in the present step includes a reference profile PRE10 that can be derived from the profile obtained from the median image. The reference profile PRE10 is additionally prepared to identify the boundary of the inner limiting membrane. The reference profile PRE10 is a typical example of the profile taken along the A-scan line extending in an area where the inner limiting membrane and an underlying pseudo-image are present. The layer boundary identifying unit 108 determines whether the detected peak coincides with the inner limiting membrane.

In the present step, the layer boundary identifying unit 108 calculates an average luminance value in a predetermined range on one side of the peak as well as in a predetermined range on the other side of the peak with reference to the profile PSA10 and the profile PMD10. More specifically, the layer boundary identifying unit 108 sets two calculation ranges having a length corresponding to ten pixels (hereinafter, referred to as peak-up B1 and peak-down B2) on both sides of the peak on the A-scan line.

Next, the layer boundary identifying unit 108 compares the calculated average luminance values to determine a relationship between them in the magnitude while taking the typical example profile into consideration. Only one condition to be satisfied with respect to the average luminance values, which can be derived from the reference profile PRE10, is peak-up B1<peak-down B2.

The layer boundary identifying unit 108 confirms whether the calculated average luminance values coincide with the interface of the inner limiting membrane by checking whether the calculated average luminance values satisfy the above-described condition.

If the above-described condition is satisfied, the layer boundary identifying unit 108 identifies the peak as the interface of the inner limiting membrane. The identified relationship is stored in the data server 113.

If the above-described condition is not satisfied, the layer boundary identifying unit 108 does not identify any retinal layer boundary along the concerned A-scan line.

(Step S708) In step S708, the layer boundary identifying unit 108 determines whether the A-scan lines located in an area including a target layer boundary to be identified have been all selected. In the determination in this step, the presence of an appropriate template is not taken into consideration.

If the processing of the flowchart illustrated in FIG. 7 is completed for all of the A-scan lines each positioned in the area including the target retinal layer boundary to be identified, the processing proceeds to step S406. If it is determined that there is at least one A-scan line that is not selected (NO in step S708), the processing proceeds to step S701.

As described above, the layer boundary identifying unit 108 determines the type of a layer boundary to be identified according to the number of edges (i.e., the feature points) detected along the A-scan line at predetermined intervals in the horizontal direction.

Thus, the layer boundary identifying unit 108 can identify the type of each layer boundary according to a change in structure or feature in an image. Further, the layer boundary identifying unit 108 can identify the position and the type of each layer boundary based on template information according to the number of feature points. Therefore, the layer boundary identifying unit 108 can identify the type and the position of each layer boundary according to a change in structure or feature in an image.

Next, example processing that can be performed by the layer boundary interpolation unit 109 in step S406 is described below with reference to the flowchart illustrated in FIG. 11. The layer boundary interpolation unit 109 performs the above-described interpolation processing for each layer boundary type.

The layer boundary interpolation unit 109 sets a search range for an unidentified part of a layer boundary whose remaining part was already identified and then identifies the position of the layer boundary in the search range.

For example, when a target layer boundary to be interpolated is the interface of the inner limiting membrane, the layer boundary interpolation unit 109 identifies the position of the inner limiting membrane at the A-scan line extending in an area where the inner limiting membrane was not identified based on positional information of the inner limiting membrane already identified by the layer boundary identifying unit 108.

(Step S1101) In step S1101, the layer boundary interpolation unit 109 selects an A-scan line extending in an area including a target portion of a layer boundary to be identified. In the present exemplary embodiment, the layer boundary interpolation unit 109 selects the A-scan line extending in an area where the position of a layer boundary was not identified in the above-described processing performed in step S405. In this case, the A-scan line extending in an area where the position of a layer boundary was not identified is the A-scan line to which no template is applicable.

(Step S1102) The layer boundary interpolation unit 109 sets a local area (hereinafter, referred to as "neighborhood area") that surrounds the A-scan line extending in an area where the position of a layer boundary was not identified. The layer boundary interpolation unit 109 performs interpolation processing based on coordinate information of the retinal layer boundary identified in the neighborhood area.

The processing to be performed in step S1102 is described below in more detail with reference to FIG. 12, in which A12 represents the A-scan line extending in the area where no retinal layer boundary was identified and R represents the neighborhood area surrounding the A-scan line A12 positioned at the center thereof. The layer boundary interpolation unit 109 performs range setting in such a way as to involve a predetermined number of A-scan lines in the neighborhood area.

The above-described neighborhood area is a rectangular area having each side comparable to nine A-scan lines (i.e., a square of 9×9 A-scan lines), in which the target A-scan line (i.e., the A-scan line extending in an area including a target layer boundary to be identified) is positioned at the center thereof.

In the neighborhood area set around the target A-scan line, if the total number of the A-scan lines along which the retinal layer boundary has already been identified is less than a predetermined number (NO in step S1102), the layer boundary interpolation unit 109 determines that the interpolation processing to be performed will become unreliable. In this case, the processing proceeds to step S1107. Namely, the layer boundary interpolation unit 109 skips the interpolation processing.

If the total number of the A-scan lines along which the retinal layer boundary has already been identified is greater than the predetermined number (YES in step S1102), then in step S1103, the layer boundary interpolation unit 109 performs the interpolation processing.

If the total number of the identification completed A-scan lines is less than the predetermined number, the layer boundary interpolation unit 109 repeats the processing of steps S1101 through S1107 to successively identify retinal layer boundaries located in the neighborhood area. When the total number of the identification completed A-scan lines exceeds the predetermined number, the layer boundary interpolation unit 109 starts the interpolation processing.

In the present exemplary embodiment, the above-described predetermined number is equal to a half of the total number of the A-scan lines that are present in the neighborhood area, i.e., 40.

(Step S1103) In step S1103, the layer boundary interpolation unit 109 calculates a feature quantity required to identify a retinal layer boundary about the A-scan line extending in an area where the position of the retinal layer boundary was not identified. The layer boundary interpolation unit 109 calculates the feature quantity based on information relating to the A-scan line along which the retinal layer boundary has already been identified.

In the present exemplary embodiment, the layer boundary interpolation unit 109 sets a local area (hereinafter, referred to as "neighborhood area") that surrounds the A-scan line along which the position of the retinal layer boundary was not identified. The layer boundary interpolation unit 109 calculates a reference position based on the retinal layer boundary already identified in the neighborhood area. As illustrated in FIG. 12, the A-scan line along which the position of the retinal layer boundary was not identified is located at the center of the neighborhood area set by the layer boundary interpolation unit 109.

The layer boundary interpolation unit 109 obtains an average z-coordinate value of each retinal layer boundary identified in the neighborhood area and designates the obtained z-coordinate position as a reference position.

The determination condition to be satisfied in executing the calculation of the reference position is similar to that used in step S402. More specifically, the layer boundary interpolation unit 109 performs the reference position calculation processing by checking whether the total number of the A-scan lines along which the retinal layer boundary has already been identified in the neighborhood area is greater than or smaller than a predetermined number.

If the reference position calculation processing is completed, the layer boundary interpolation unit 109 determines an image area that can be regarded as including the layer boundary based on the calculated reference position of each layer as a search range. The layer boundary interpolation unit 109 identifies the retinal layer boundary that corresponds to the A-scan line in the above-described search range.

The layer boundary interpolation unit 109 sets a predetermined range in the depth direction, as a search range for the retinal layer boundary, using the average z-coordinate value of each retinal layer that has been calculated as the reference position. For example, the predetermined range in the depth direction set by the layer boundary interpolation unit 109 includes an upper range corresponding to five pixels set on the upper side of the average z-coordinate value and a lower range corresponding to five pixels set on the lower side of the average z-coordinate value.

As described above, the layer boundary interpolation unit 109 refers to a depth directional position of a layer boundary whose position has already been identified by the layer boundary identifying unit 108 to set a search range for a portion of the layer boundary whose position was not identified the layer boundary identifying unit 108.

The search range setting is not limited to the above-described example and any other appropriate setting can be employed. For example, if an image includes a small amount of noises, the layer boundary identification processing can be performed accurately by setting a greater search range.

Further, if the structure of a layer is comparatively simple and flat, it is unnecessary to set a greater search range. Therefore, it may be useful to change the search range with reference to structural information of peripheral layers. Further, when the isotropy of noises is taken into consideration, it may be useful to locally separate noises from signal components by extracting noise components from the entire image or along an A-scan line to be processed.

(Step S1104) In step S1104, the layer boundary interpolation unit 109 searches for a peak area along the profile of the Sobel image A within the search range. In this case, the peak area is an area in the vicinity of a local maximum value that is equal to or greater than a predetermined value in the profile of the Sobel image A.

The peak area corresponds to an area where the luminance change in a tomography image exceeds a predetermined threshold value. The above-described predetermined threshold value corresponds to a second threshold value according to the present invention.

As the layer boundary interpolation unit 109 can set a narrower search range to effectively perform peak search processing, the layer boundary interpolation unit 109 can find a smaller peak area with a threshold value that is smaller than the first threshold value set by the detection unit 106 in step S404.

Further, as the layer boundary interpolation unit 109 can set a search range based on an average value of the depth directional position of the layer boundary already identified in the neighborhood area, the possibility that the layer boundary is present in the search range set by the layer boundary interpolation unit 109 is higher.

(Step S1105) The layer boundary interpolation unit 109 determines whether the peak area is present. If the peak area is present, the layer boundary interpolation unit 109 determines that the position of the target layer boundary to be interpolated can be identified. Therefore, the processing proceeds to step S1106 in which the layer boundary interpolation unit 109 continues the interpolation processing.

If no peak area is present, the layer boundary interpolation unit 109 determines that the reliability of the interpolation processing if performed becomes lower. Therefore, the layer boundary interpolation unit 109 skips the interpolation processing. The processing proceeds to step S1107.

If there is not any peak area detected in step S1105, the layer boundary interpolation unit 109 may identify a position where the edge component of the Sobel image A becomes largest in the search range as a retinal layer boundary.

(Step S1106) The layer boundary interpolation unit 109 identifies the position of the peak area having a largest luminance change as the position of the target boundary.

(Step S1107) The layer boundary interpolation unit 109 determines whether the above-described layer boundary identification processing has been completed for all of the A-scan lines located in the area where the target layer boundary to be identified is present.

If the layer boundary interpolation unit 109 determines that there is at least one A-scan line not subjected to the above-described layer boundary identification processing, the processing returns to step S1101 in which the layer boundary interpolation unit 109 repeats the interpolation processing.

In this case, the layer boundary interpolation unit 109 newly sets a search range for a layer portion whose position was not identified, based on the depth directional position of a layer boundary whose position has already been identified by the layer boundary identifying unit 108 or the layer boundary interpolation unit 109.

Then, the layer boundary interpolation unit 109 further identifies the position of the layer boundary portion whose position was not identified, based on a luminance change in the depth direction within the newly set search range. The layer boundary interpolation unit 109 repetitively performs the above-described processing to successively identify an unidentified portion of the layer boundary, with reference to the closest identified portion of the layer boundary.

If the above-described layer boundary identification processing is completed for all target A-scan lines, the layer boundary interpolation unit 109 terminates the processing of the flowchart illustrated in FIG. 11. Alternatively, the layer boundary interpolation unit 109 may terminate the processing of the flowchart illustrated in FIG. 11 if the processing time exceeds a predetermined time or when the total number of the repetitively performed loop processing exceeds a predetermined value.

Moreover, the total number of the A-scan lines having been subjected to the above-described layer boundary identification processing may not change even after the layer boundary interpolation unit 109 has performed the loop processing of steps S1101 to S1107 a predetermined number of times. In such a case, the layer boundary interpolation unit 109 can forcibly terminate the processing of the flowchart illustrated in FIG. 11.

As described above, the layer boundary interpolation unit 109 determines a search range based on the depth directional position of the already identified layer boundary and identifies the position of an unidentified portion of the layer boundary based on a luminance change in the search range having been set.

Thus, the present exemplary embodiment can improve the accuracy of the layer boundary identification processing compared to a case where the layer boundary identification processing is performed based on a luminance change in the entire range of the A-scan line.

Further, the layer boundary interpolation unit 109 can set a narrower search range and can set a smaller threshold value to be used to search for a peak. Thus, the layer boundary interpolation unit 109 can identify the position of an unidentified portion of the layer boundary based on a smaller luminance change.

As described above, the image processing apparatus according to the present exemplary embodiment calculates a luminance value and a boundary position of each retinal layer in the neighborhood area, in the processing to be performed to identify a retinal layer boundary included in a tomography image of an eye to be examined.

Then, the image processing apparatus according to the present exemplary embodiment sets conditions to be satisfied to perform retinal layer boundary identification processing based on the obtained information. Thus, the image processing apparatus 101 can accurately perform the retinal layer boundary identification processing even when the luminance value or the layer structure of a target retinal layer is changed.

For example, according to the OCT, the profile of the same retinal layer may change greatly depending on a portion to be examined. Even when such a change occurs in the luminance value, the image processing apparatus according to the present exemplary embodiment can set appropriate retinal layer boundary identification conditions for a target layer portion to be identified referring to the information of each retinal layer obtainable in the neighborhood area and can accurately identify the position of the retinal layer boundary.

Further, the image processing apparatus according to the present exemplary embodiment can set appropriate retinal layer boundary identification conditions from an input image, without performing manual adjustment of the threshold value, while taking individual differences and machine model differences in the tendency of the luminance value into consideration.

Accordingly, the image processing apparatus according to the present exemplary embodiment can eliminate errors in identifying the type of each layer boundary even when different types of later structures appear in an optical coherence tomography image of an eye to be examined.

In a second exemplary embodiment, the present invention is applied to identification of the interface of the nerve fiber layer, the interface of the inner plexiform layer, and the interface of the outer plexiform layer.

Further, the present exemplary embodiment includes processing to be performed to determine whether the profile of an image coincides with template information when the template information is selected. The template selection unit 107 can serve as the above-described determination unit. It may also be desired to provide a circuit capable of functionally operable as the determination unit.

In the present exemplary embodiment, it is presumed that the interface of the inner limiting membrane and the interface between inner and outer segments of the photoreceptors are identified beforehand. The present exemplary embodiment includes preparing a reference profile that represents a layer structure for each of the nerve fiber layer, the inner plexiform layer, and the outer plexiform layer. The present exemplary embodiment further includes selecting an optimum reference profile to be used to identify each retinal layer boundary with reference to the number of feature points obtained from the profile of the Sobel image B.

The present exemplary embodiment includes processing to be performed to determine whether the selected template is appropriate with reference to luminance values obtained in upper and lower areas of a luminance change peak position. Respective retinal layers are different from each other in reflectance. Therefore, accurately identifying each layer boundary and the type of the detected layer are feasible based on the luminance values of the above-described layer areas. An image processing system according to the present exemplary embodiment is similar to that described in the first exemplary embodiment and therefore its description is not repeated.

Figure 13:
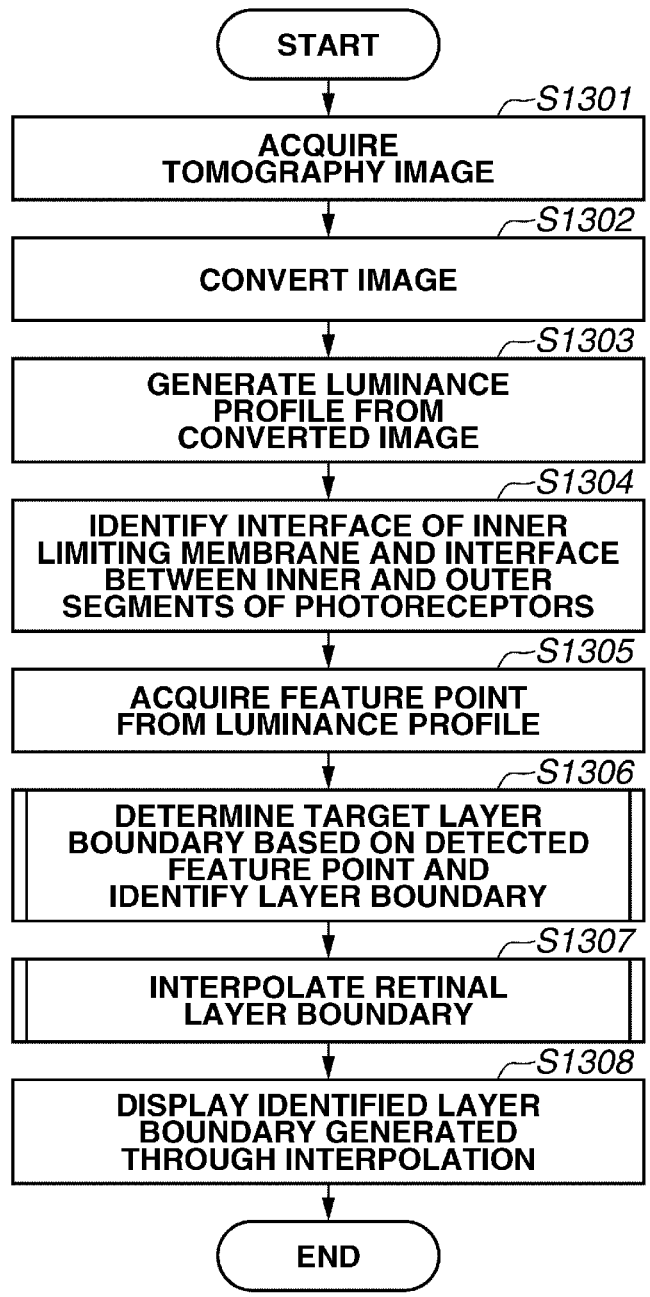
FIG. 13 is a flowchart illustrating an example flow of processing that can be performed by the image processing apparatus according to a second exemplary embodiment of the present invention.

An example flow of processing that can be performed by the image processing apparatus 101 according to the present exemplary embodiment is described below with reference to a flowchart illustrated in FIG. 13. The processing in FIG. 13 includes a portion similar to the processing described in the first exemplary embodiment and therefore its description is not repeated.

(Step S1304) In step S1304, the image processing apparatus 101 identifies the interface of the inner limiting membrane and the interface between inner and outer segments of the photoreceptors. The image processing apparatus 101 can perform the above-described identification processing using the method described in the first exemplary embodiment or using another method.

For example, the image processing apparatus 101 acquires a tomography image in which the position of the above-described layer boundary is identified beforehand. Then, the image processing apparatus 101 can perform the above-described identification processing based on the identified position data.

The image processing apparatus 101 identifies the interface of the nerve fiber layer, the interface of the inner plexiform layer, and the interface of the outer plexiform layer based on the above-described positions of the interface of the inner limiting membrane and the interface between inner and outer segments of the photoreceptors.

(Step S1306) In step S1306, the template selection unit 107 selects template information and the layer boundary identifying unit 108 performs layer boundary identification processing. The present exemplary embodiment is different from the first exemplary embodiment in performing processing to determine whether the selected template information matches with the profile of the tomography image, after the template selection processing is completed, as described below in more detail.

(Step S1307) In step S1307, the image processing apparatus 101 performs interpolation processing on a layer boundary that was not identified in step S1306 to interpolate the position of the unidentified layer boundary. The processing to be performed in step S1307 is different from the processing described in the first exemplary embodiment in identifying a peak position of a peak area that is closest to the calculated average Z-coordinate, among peak areas discovered in the search range, as the position of the layer boundary, as described below in more detail.

Figure 14:
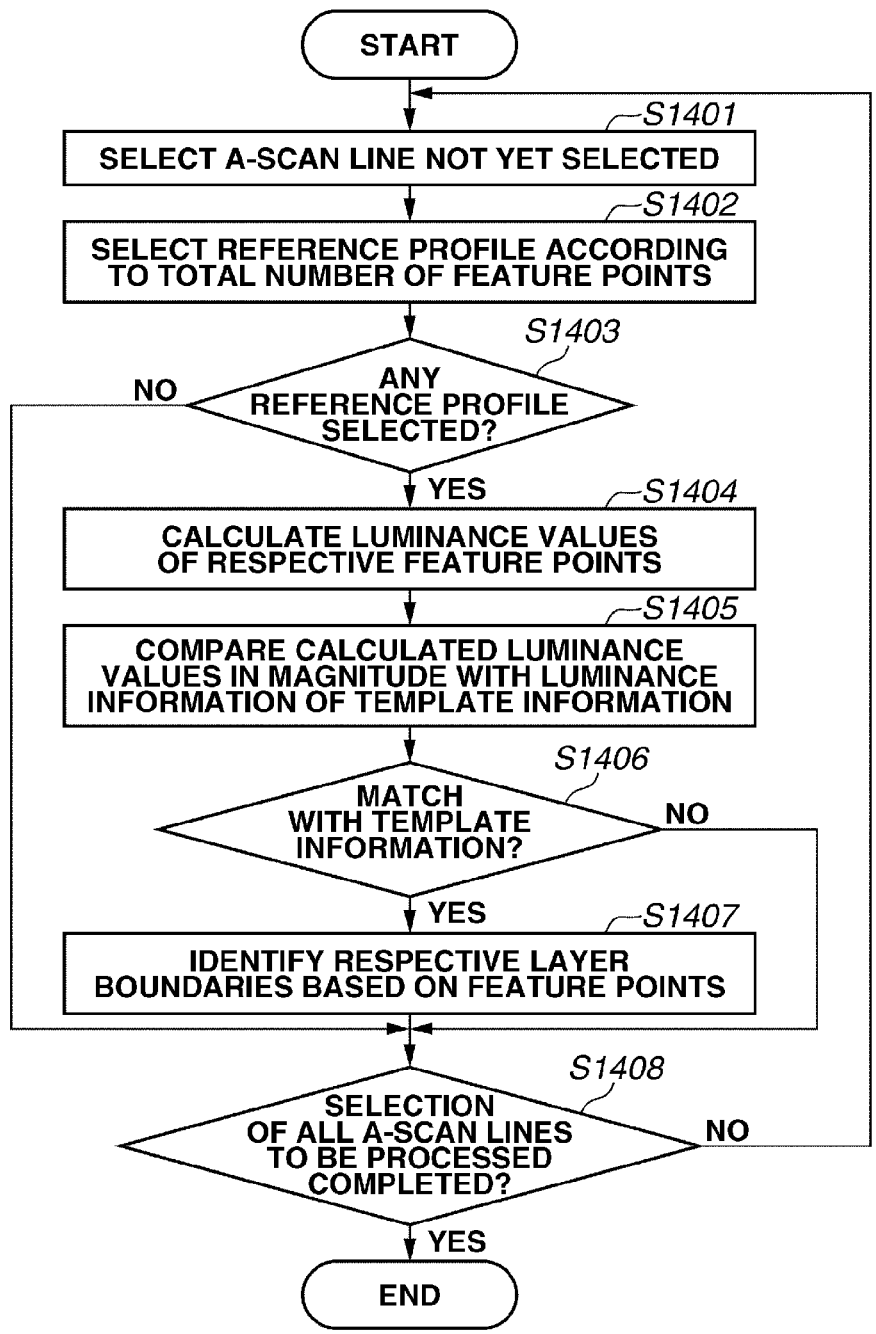
FIG. 14 is a flowchart illustrating an example flow of processing that can be performed by the template selection unit and the layer boundary identifying unit according to the second exemplary embodiment of the present invention.

An example flow of the processing to be performed by the template selection unit 107 and the layer boundary identifying unit 108 in step S1306 is described below with reference to the flowchart of FIG. 14. The processing in FIG. 14 includes a portion similar to the processing described in the first exemplary embodiment and therefore its description is not repeated.

Figure 15:
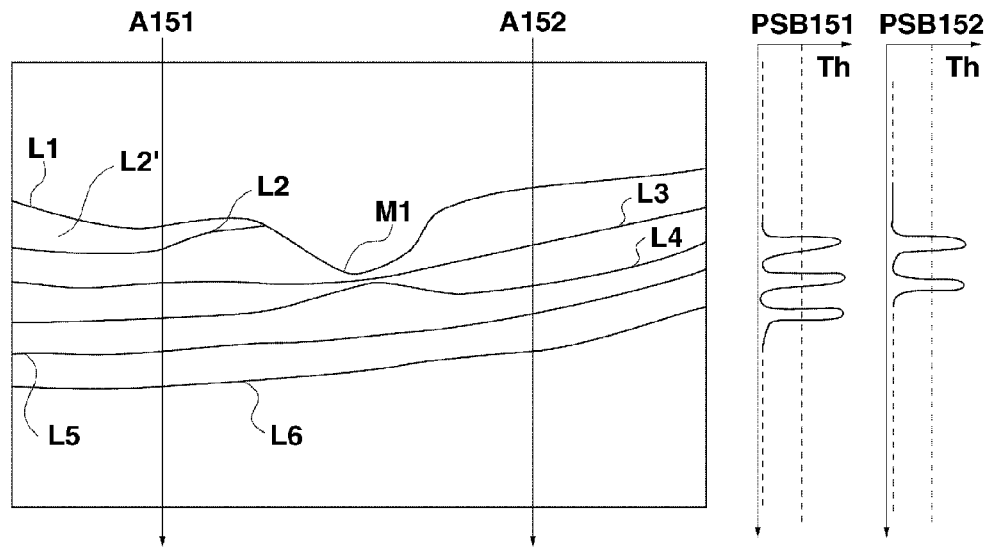
FIG. 15 schematically illustrates example processing that can be performed by the template selection unit according to the second exemplary embodiment of the present invention.

(Step S1402) Processing to be performed in step S1402 contains all of the processing performed in steps S702, S703, S705, and S706 described in the first exemplary embodiment. The processing to be performed in step S1402 is described below in more detail with reference to FIG. 15. FIG. 15 illustrates an example tomography image of retinal layers, in which vertical lines A151 and A152 represent two A-scan lines. The tomography image illustrated in FIG. 15 further includes profiles PSB151 and PSB152 obtained from the Sobel image B.

The depth directional range of the profile to be used in the layer structure determination processing has an upper edge and a lower edge that correspond to the interface of the inner limiting membrane and the interface between inner and outer segments of the photoreceptors that are identified beforehand, respectively. Therefore, the layer structure determination processing is performed only in the range indicated by solid lines of the profiles PSB151 and PSB152 illustrated in FIG. 15.

To estimate each retinal layer, the template selection unit 107 counts the number of peaks appearing along the profile in the range extending from the inner limiting membrane to the interface between inner and outer segments of the photoreceptors. The nerve fiber layer may not be included in an image if the position of a selected A-scan line is inappropriate (see the profile PSB152 illustrated in FIG. 15).

Considering the above-described situation, the template selection unit 107 counts the number of peaks along the profile of the Sobel image B in each A-scan line and, if the number of detected peaks is three, the template selection unit 107 determines that there is a higher possibility that the nerve fiber layer, the inner plexiform layer, and the outer plexiform layer are present along the target A-scan line.

The above-described each layer is a layer boundary or a candidate of the layer that exists at a position corresponding to the A-scan line (processing target) and the peak position is a candidate of the position of the above-described each layer. Thus, in this case, the template selection unit 107 selects a reference profile employable when the number of peaks is three.

If the number of detected peaks is two, the template selection unit 107 determines that there is a higher possibility that the inner plexiform layer and the outer plexiform layer are present along the target A-scan line. The above-described each layer is a candidate of the layer that exists at a position corresponding to the A-scan line (processing target) and the peak position is a candidate of the position of the above-described each layer. Thus, in this case, the template selection unit 107 selects a reference profile employable when the number of peaks is two.

In the present exemplary embodiment, the image used in the above-described layer boundary identification processing is the Sobel image B. The above-described Sobel image B is an image that can be obtained by extracting each lower-side edge at which the luminance value changes from a larger side to a lower side in the depth direction.

(Step S1403) In step S1403, the template selection unit 107 determines whether the reference profile has been selected for the A-scan line (i.e., the processing target). If it is determined that the reference profile has been selected (YES in step S1403), the template selection unit 107 can perform layer boundary identification processing. Therefore, the processing proceeds to step S1404.

If no reference profile has been selected (NO in step S1403), the template selection unit 107 determines that the layer boundary identification processing is unfeasible due to the presence of noise. Therefore, the processing proceeds to step S1408 in which the template selection unit 107 starts template selection processing for the next A-scan line.

(Step S1404) The determination unit determines whether the template selected in step S1403 matches the A-scan line to be processed. To this end, in step S1404, the determination unit calculates luminance values of respective feature points.

(Step S1405) In step S1405, the determination unit compares the calculated luminance values of respective feature points in the magnitude with luminance information of the reference profile (i.e., the template information).

(Step S1406) In step S1406, the determination unit determines whether the template information matches the A-scan line to be processed based on the above-described comparison result. If the template information matches the A-scan line to be processed (YES in step S1406), the determination unit determines that the layer boundary identification processing is feasible. Therefore, the processing proceeds to step S1407.

If the template information does not match the A-scan line to be processed (NO in step S1406), the determination unit determines that the template determination is unfeasible. Therefore, the image processing apparatus 101 skips the identification processing. The processing proceeds to step S1408.

The processing to be performed in step S1407 and step S1408 is similar to the processing described in the first exemplary embodiment and therefore its description is not repeated. Hereinafter, the processing to be performed in steps S1404 to S1406 is described below in more detail.

Figure 16:
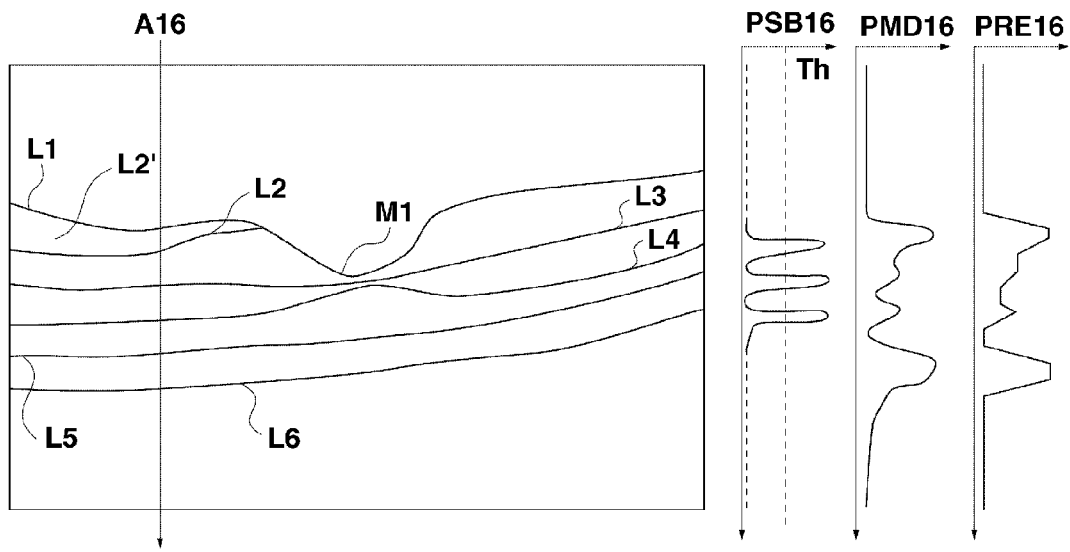
FIG. 16 schematically illustrates example processing that can be performed by a determination unit according to the second exemplary embodiment of the present invention.

Example processing to be performed when the number of detected feature points is three is described below in more detail with reference to FIG. 16. FIG. 16 illustrates an example tomography image of retinal layers, in which a vertical line A16 represents one of the A-scan lines. The tomography image illustrated in FIG. 16 further includes a profile PSB16 obtained from the Sobel image B and a profile PMD16 obtained from the median image.

Further, a plurality of profiles used in the present step includes a reference profile PRE16 that can be derived from the profile obtained from the median image. The reference profile PRE16 is additionally prepared to identify each boundary of the target three layers (i.e., the nerve fiber layer, the inner plexiform layer, and the outer plexiform layer).

The reference profile PRE16 is a typical example of the profile taken along the A-scan line extending in an area where the nerve fiber layer, the inner plexiform layer, and the outer plexiform layer are present.

In the present exemplary embodiment, the typical example indicates a tendency of the luminance between respective layers along the A-scan line extending in an area where the target three layers (i.e., the nerve fiber layer, the inner plexiform layer, and the outer plexiform layer) are present, in which no noise is present.

For example, it is experimentally known that the luminance value of the nerve fiber layer tends to be higher than those of the inner plexiform layer and the outer plexiform layer. Therefore, the prepared profile PRE16 possesses the above-described tendency in the luminance features.

The reference profile PRE16 is not limited to the above-described example. Any other profile can be employed if the luminance tendency of each retinal layer and a positional relationship between retinal layers can be identified based on the employed profile.

The reference profile PRE16 does not reflect the thickness of each retinal layer, although the thickness is generally variable depending on the position of the A-scan line. Therefore, the reference profile PRE16 is employable for any A-scan line extending in an area where the target three layers (i.e., the nerve fiber layer, the inner plexiform layer, and the outer plexiform layer) are present.

The determination unit uses the reference profile PRE16 to determine whether the detected three peaks coincide with the above-described three layers (i.e., the nerve fiber layer, the inner plexiform layer, and the outer plexiform layer).

First, the determination unit calculates an average luminance value between respective peaks appearing on the profile PSB16. The determination unit uses, as a luminance value, a value of the profile PMD16 corresponding to the position of the profile PSB16. The determination unit refers to three peaks of the profile PSB16 as a first peak, a second peak, and a three peak, respectively, which are positioned in this order from the shallow side.

The range in which the determination unit calculates the average luminance value is a range extending from the inner limiting membrane to the first peak, a range extending from the first peak to the second peak, a range extending from the second peak to the third peak, and a range extending from the third peak to the interface between inner and outer segments of the photoreceptors.

The above-described ranges are successively referred to as peak-to-peak A1, peak-to-peak A2, peak-to-peak A3, and peak-to-peak A4. Further, the range "peak-to-peak A3" (i.e., the range extending from the second peak to the third peak) includes two equally divided ranges. One of the above-described two divided ranges, which is adjacent to the second peak, is referred to as "peak-to-peak A31." The other of the above-described two divided ranges, which is adjacent to the third peak, is referred to as "peak-to-peak A32." The determination unit calculates average luminance values in the above-described ranges using the profile PMD16.

Next, the determination unit compares the calculated average luminance values to determine a relationship between them in the magnitude while taking the reference profile PRE16 into consideration. Conditions to be satisfied with respect to the average luminance values, which can be derived from the reference profile PRE16, are peak-to-peak A1>peak-to-peak A2, peak-to-peak A1>peak-to-peak A3, peak-to-peak A3>peak-to-peak A4, and peak-to-peak A31<peak-to-peak A32.

The determination unit confirms whether the calculated average luminance values coincide with the target three layers (i.e., the nerve fiber layer, the inner plexiform layer, and the outer plexiform layer) by checking whether the calculated average luminance values satisfy the above-described conditions.

If the above-described conditions are all satisfied, the determination unit identifies the first peak, the second peak, and the third peak as boundaries of the nerve fiber layer, the inner plexiform layer, and the outer plexiform layer. The identified relationship is stored in the data server 113.

If at least one of the above-described conditions is not satisfied, the determination unit does not identify any retinal layer boundary along the concerned A-scan line.

Figure 17:
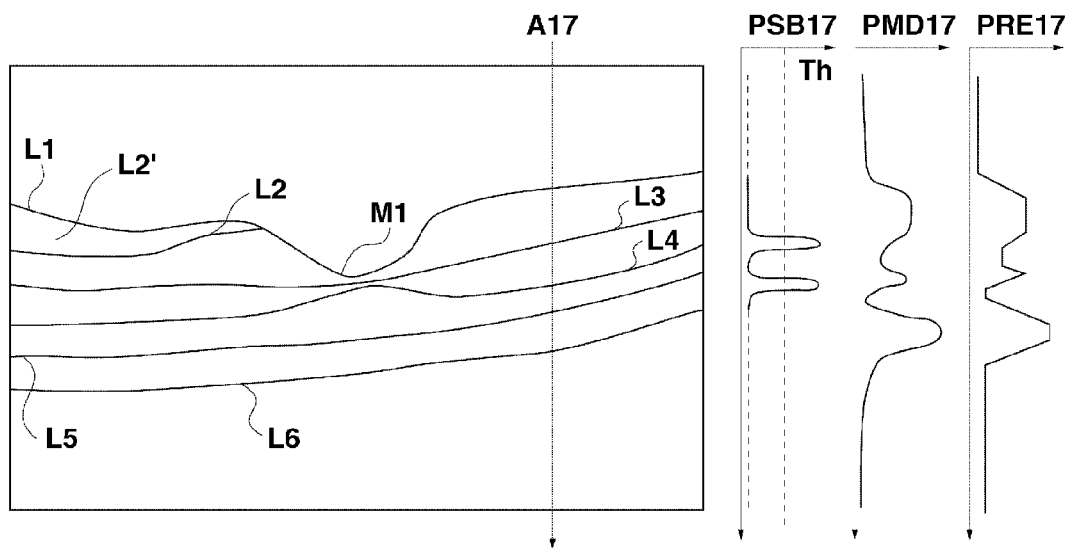
FIG. 17 schematically illustrates example processing that can be performed by the determination unit according to the second exemplary embodiment of the present invention.

Example processing to be performed when the number of detected feature points is two is described below in more detail with reference to FIG. 17. FIG. 17 illustrates an example tomography image of retinal layers, in which a vertical line A17 represents one of the A-scan lines. The tomography image illustrated in FIG. 17 further includes a profile PSB17 obtained from the Sobel image B and a profile PMD17 obtained from the median image.

Further, a plurality of profiles used in the present step includes a reference profile PRE17 that can be derived from the profile obtained from the median image. The reference profile PRE17 is additionally prepared to identify each boundary of the target two layers (i.e., the inner plexiform layer and the outer plexiform layer).

The reference profile PRE17 is a typical example of the profile taken along the A-scan line extending in an area where the inner plexiform layer and the outer plexiform layer are present.

Similar to the description in step S1402, the typical example indicates a tendency of the luminance between respective layers along the A-scan line extending in an area where the target two layers (i.e., the inner plexiform layer and the outer plexiform layer) are present, in which no noise is present.

Therefore, the reference profile PRE17 is employable for any A-scan line extending in an area where the target two layers are present. The determination unit uses the reference profile PRE17 to determine whether the detected two peaks coincide with the inner plexiform layer and the outer plexiform layer.

In the present step, the determination unit calculates an average luminance value between respective peaks using the profile PSB17 and the profile PMD17. The determination unit refers to two peaks of the profile PSB17 as a first peak and a second peak, respectively, which are positioned in this order from the shallow side.

The range in which the determination unit calculates the average luminance value is a range extending from the inner limiting membrane to the first peak, a range extending from the first peak to the second peak, and a range extending from the second peak to the interface between inner and outer segments of the photoreceptors.

The above-described ranges are successively referred to as peak-to-peak B1, peak-to-peak B2, and peak-to-peak B3. Further, the range "peak-to-peak B2" (i.e., the range extending from the first peak to the second peak) includes two equally divided ranges. One of the above-described two divided ranges, which is adjacent to the first peak, is referred to as "peak-to-peak B21." The other of the above-described two divided ranges, which is adjacent to the second peak, is referred to as "peak-to-peak B22." The determination unit calculates average luminance values in the above-described ranges using the profile PMD17.

Next, the determination unit compares the calculated average luminance values to determine a relationship between them in the magnitude while taking the typical example profile into consideration. Conditions to be satisfied with respect to the average luminance values, which can be derived from the reference profile PRE17, are peak-to-peak B1>peak-to-peak B2, peak-to-peak B2>peak-to-peak B3, and peak-to-peak B21<peak-to-peak B22.

The determination unit confirms whether the calculated average luminance values coincide with the target two layers (i.e., the inner plexiform layer and the outer plexiform layer) by checking whether the calculated average luminance values satisfy the above-described conditions.

If the above-described conditions are all satisfied, the determination unit identifies the first peak and the second peak as boundaries of the inner plexiform layer and the outer plexiform layer. The identified relationship is stored in the data server 113.

If at least one of the above-described conditions is not satisfied, the determination unit does not identify any retinal layer boundary along the concerned A-scan line.

As described above, determining whether a template selected according to the total number of detected feature points coincides with a profile taken along a target A-scan line to be processed is useful to eliminate errors in the layer boundary identification processing that may be derived from an error in template selection. Further, using luminance values of inter-boundary areas in appropriately determining the template information is useful to eliminate errors in the layer boundary identification processing.

An image processing system according to a third exemplary embodiment includes an algorithm switching unit configured to select an optimum algorithm based on pattern matching between profiles, without counting the number of peaks appearing along a profile obtained from the Sobel image.

More specifically, an image processing apparatus adjusts a positional relationship between a target profile of a median image to be processed and each reference profile and calculates a distance between corresponding signals. Then, the image processing apparatus selects an optimum algorithm to be used in retinal layer boundary identification with reference to the layer structure of a reference profile which is smallest in the cumulative value of the calculated distance. In the present exemplary embodiment, an example algorithm switching to be performed by the image processing apparatus to identify the nerve fiber layer, the inner plexiform layer, and the outer plexiform layer is described below.

Figure 18:
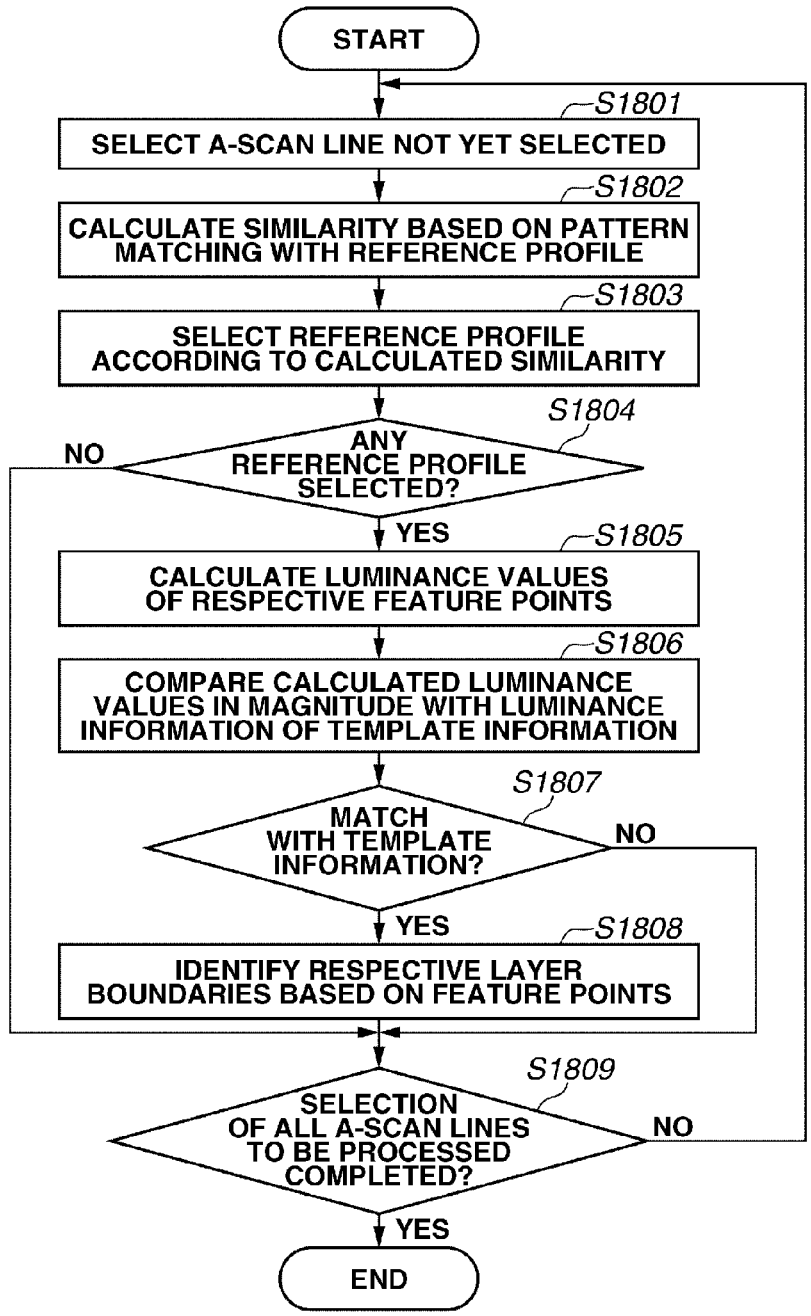
FIG. 18 is a flowchart illustrating an example flow of processing that can be performed by the image processing apparatus according to a third exemplary embodiment of the present invention.

An example flow of processing that can be performed by the template selection unit 107 and the layer boundary identifying unit 108 according to the present exemplary embodiment is described below with reference to the flowchart illustrated in FIG. 18. The flowchart in FIG. 18 includes a portion similar to the processing described in the second exemplary embodiment with reference to the flowchart illustrated in FIG. 14 and therefore its description is not repeated.

(Step S1802) In step S1802, the template selection unit 107 calculates a similarity between the target profile and each of all reference profiles along each A-scan line. Then, the template selection unit 107 selects an algorithm based on the calculated similarity. In the present exemplary embodiment, the template selection unit 107 can use a pattern matching method to calculate the above-described similarity based on a comparison between profiles. An example calculation method is described below.

Figure 19:
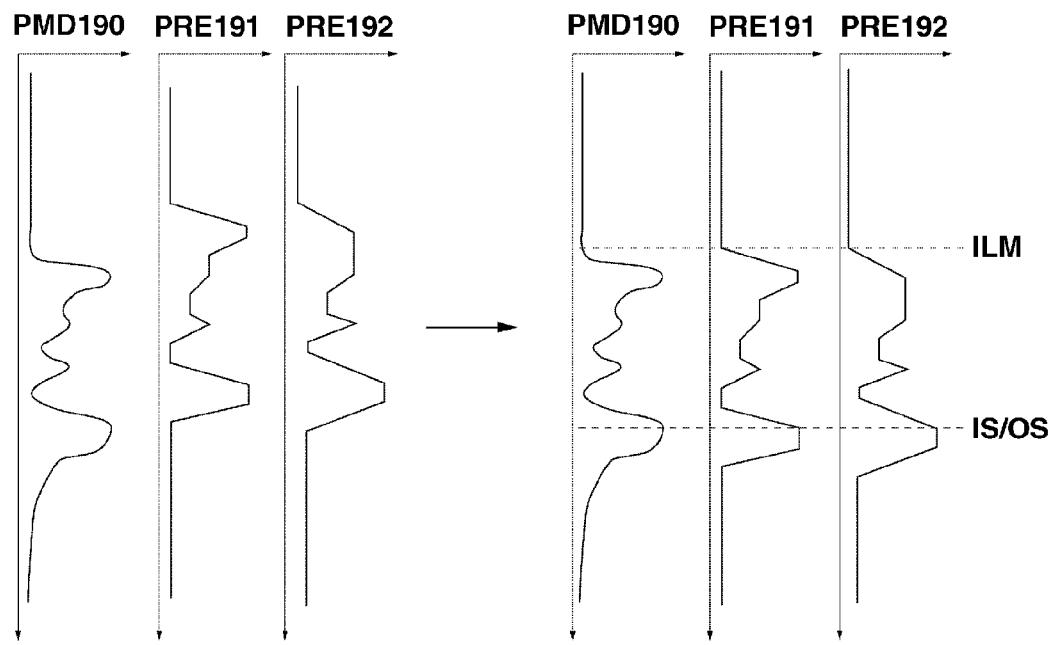
FIG. 19 schematically illustrates example pattern matching processing that can be performed by the template selection unit according to the third exemplary embodiment of the present invention.

Example processing is described below in more detail with reference to FIG. 19. A tomography image illustrated in FIG.

19 includes one A-scan line A19 and a profile PMD190 obtained from the median image. The tomography image illustrated in FIG. 19 further includes a reference profile PRE191 that can be obtained when three layers of the nerve fiber layer, the inner plexiform layer, and the outer plexiform layer are present. The tomography image illustrated in FIG. 19 further includes a reference profile PRE192 that can be obtained when two layers of inner plexiform layer and the outer plexiform layer are present.

First, the template selection unit 107 adjusts the positional relationship between a median image profile taken along the target A-scan line to be processed and each reference profile. The template selection unit 107 can perform the above-described positioning processing with reference to the positions of the inner limiting membrane and the interface between inner and outer segments of the photoreceptors, which have already been identified in step S1406 or its preceding step.

The template selection unit 107 expands or contracts the reference profile PRE191 and the reference profile PRE192 in such a way as to adjust the positions of the inner limiting membrane and the interface between inner and outer segments of the photoreceptors with corresponding positions of the profile PMD190.

Figure 20:
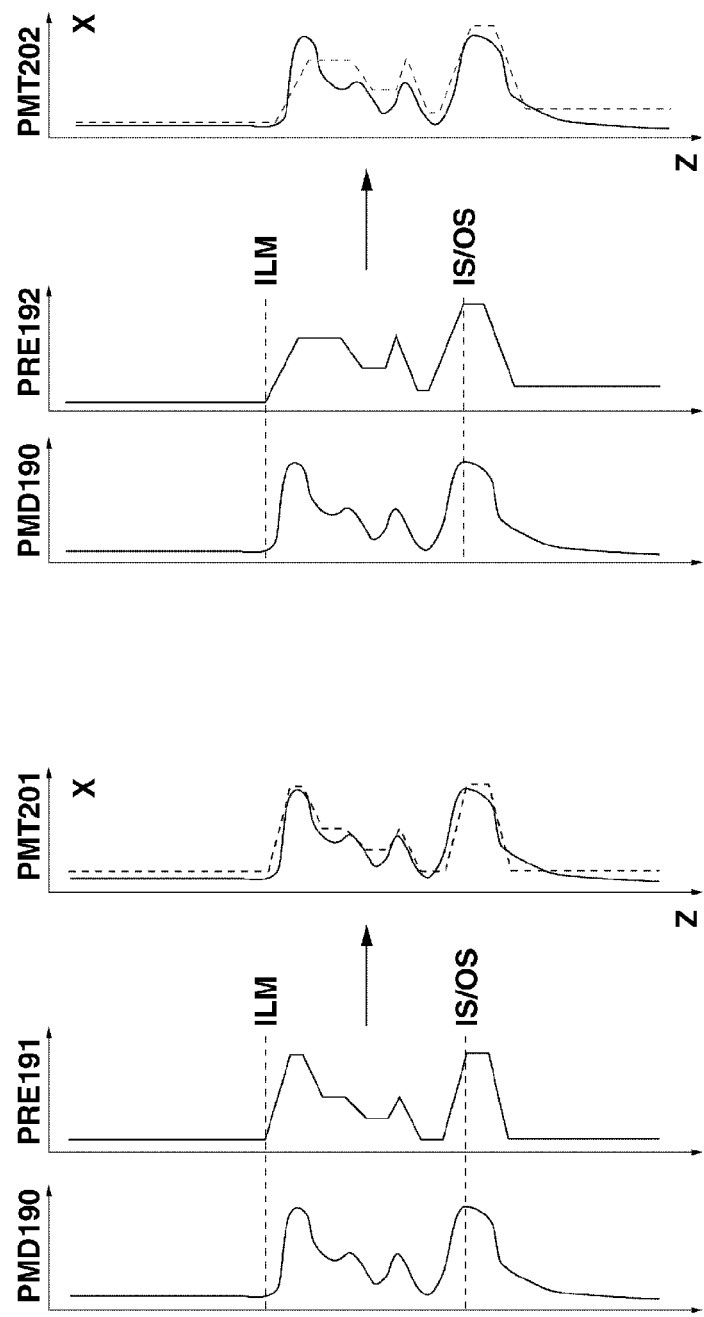
FIG. 20 schematically illustrates example pattern matching processing that can be performed by the template selection unit according to the third exemplary embodiment of the present invention.

Then, the template selection unit 107 overlaps each of the reference profile PRE191 and the profile PRE192 with the profile PMD190, as indicated by profiles PMT201 and PMT202 illustrated in FIG. 20. Further, the template selection unit 107 calculates the distance between the overlapped profiles at each corresponding point.

In the present exemplary embodiment, the distance calculated by the template selection unit 107 is a difference in the x-coordinate direction between the overlapped profiles measured at the same z-coordinate position. The template selection unit 107 obtains a cumulative value of the above-described distance for each reference profile.

(Step S1803) In step S1803, the template selection unit 107 selects an optimum template with reference to the calculated similarity. In the present exemplary embodiment, the template selection unit 107 selects a template that fits the structure of the reference profile having a lowest cumulative value (i.e., highest similarity).

The selected template information is associated with position/type information of a layer boundary. Therefore, the template selection unit 107 can determine the type of a layer boundary (processing target) to be identified along the A-scan line. In the present exemplary embodiment, if it is determined that there is a higher similarity between the profile PMD190 and the reference profile PRE191, the template selection unit 107 determines that the nerve fiber layer, the inner plexiform layer, and the outer plexiform layer are present along the A-scan line. Then, the processing proceeds to step S1804.

As described above, the image processing apparatus according to the present exemplary embodiment selects an optimum template based on the pattern matching processing and identifies the position and the type of each layer boundary based on template information. Therefore, the image processing apparatus according to the present exemplary embodiment can identify the type and the position of each layer boundary according to a change in the structure or the feature of an image.

If the calculated similarity is high when the template selection is performed based on the pattern matching as described in the present exemplary embodiment, it is unnecessary to perform the adaptability determination processing described in the second exemplary embodiment. In general, when the calculated similarity is high, it can be regarded that the compared profiles substantially coincide with each other.

In this case, the processing can be simplified because the image processing apparatus is not required to perform the above-described selection processing based on the number of detected feature points and can skip the subsequent determination processing.

On the other hand, in the second exemplary embodiment, it may be useful to perform the pattern matching processing according to the present exemplary embodiment as adaptability determination processing to be performed by the determination unit. In this case, the determination unit performs the determination processing by checking whether the calculated similarity exceeds a predetermined threshold value.

Further, the template to be used in the present exemplary embodiment can be a reference profile itself that can be created with reference to the average (or median) of a profile of a tomography image of layer boundaries having been identified beforehand.

A fourth exemplary embodiment is characterized in that, in the interpolation processing to be performed by the layer boundary interpolation unit 109, a position that is closest to an average depth directional value of the identification completed layer boundary, among luminance change peaks in the search range, is identified as the position of the layer boundary.

The image processing apparatus according to the present exemplary embodiment performs interpolation processing on the interface of the nerve fiber layer, the interface of the inner plexiform layer, and the interface of the outer plexiform layer in the following manner.

Figure 21:
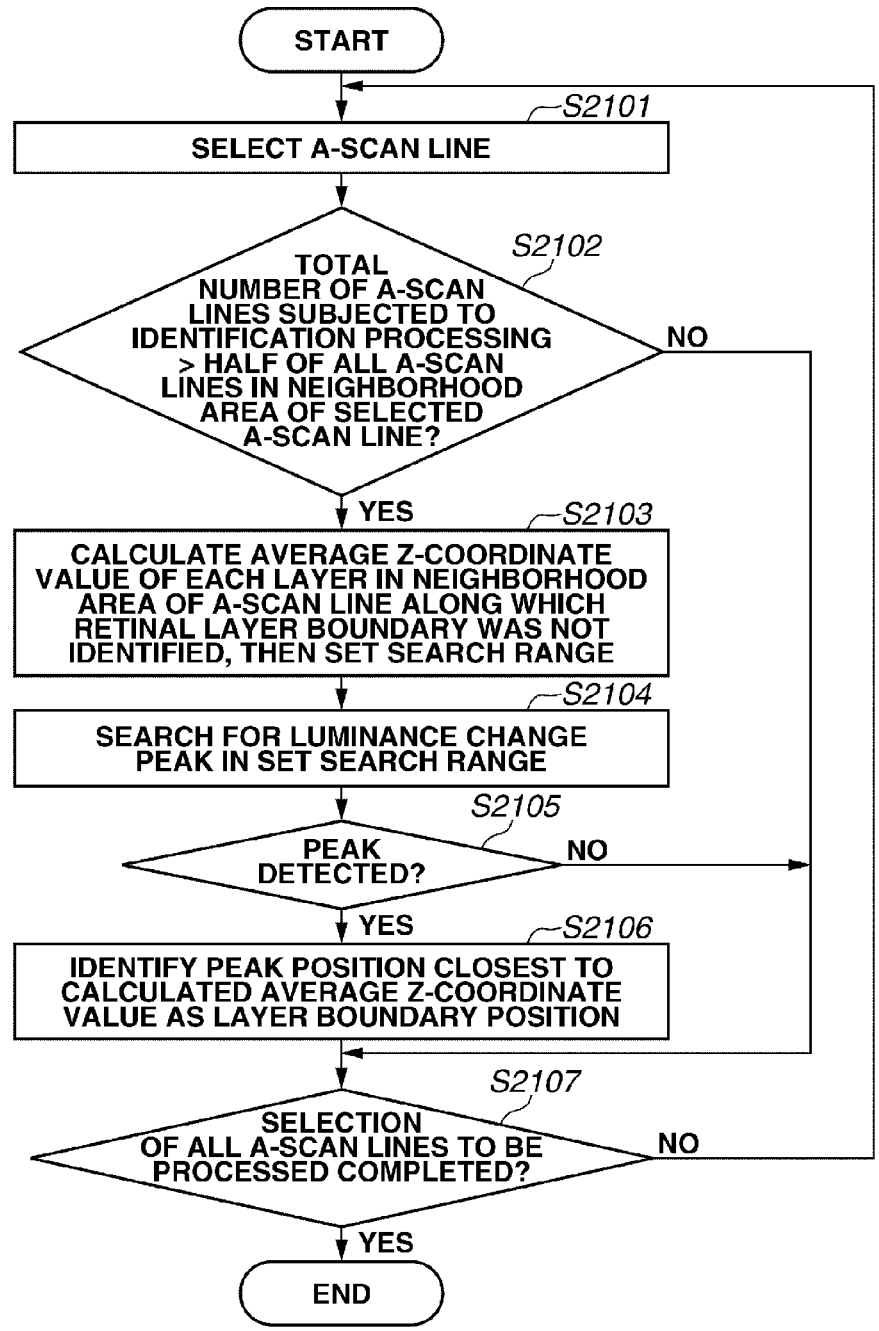
FIG. 21 is a flowchart illustrating an example flow of processing that can be performed by the layer boundary interpolation unit according to a fourth exemplary embodiment of the present invention.

FIG. 21 is a flowchart illustrating example retinal layer boundary interpolation processing according to the present exemplary embodiment. The flowchart illustrated in FIG. 21 includes a portion similar to the processing described in the first exemplary embodiment with reference to the flowchart illustrated in FIG. 11 and therefore its description is not repeated.

(Step S2103) In step S2103, the layer boundary interpolation unit 109 calculates a feature quantity required to identify a retinal layer boundary about the A-scan line extending in an area where the position of the retinal layer boundary was not identified. The layer boundary interpolation unit 109 calculates the feature quantity based on information relating to the A-scan line along which the retinal layer boundary has already been identified.

In the present exemplary embodiment, the layer boundary interpolation unit 109 sets a local area (hereinafter, referred to as "neighborhood area") that surrounds the A-scan line along which the position of the retinal layer boundary was not identified. The layer boundary interpolation unit 109 calculates a feature quantity based on the retinal layer boundary already identified in the neighborhood area.

Figure 12:
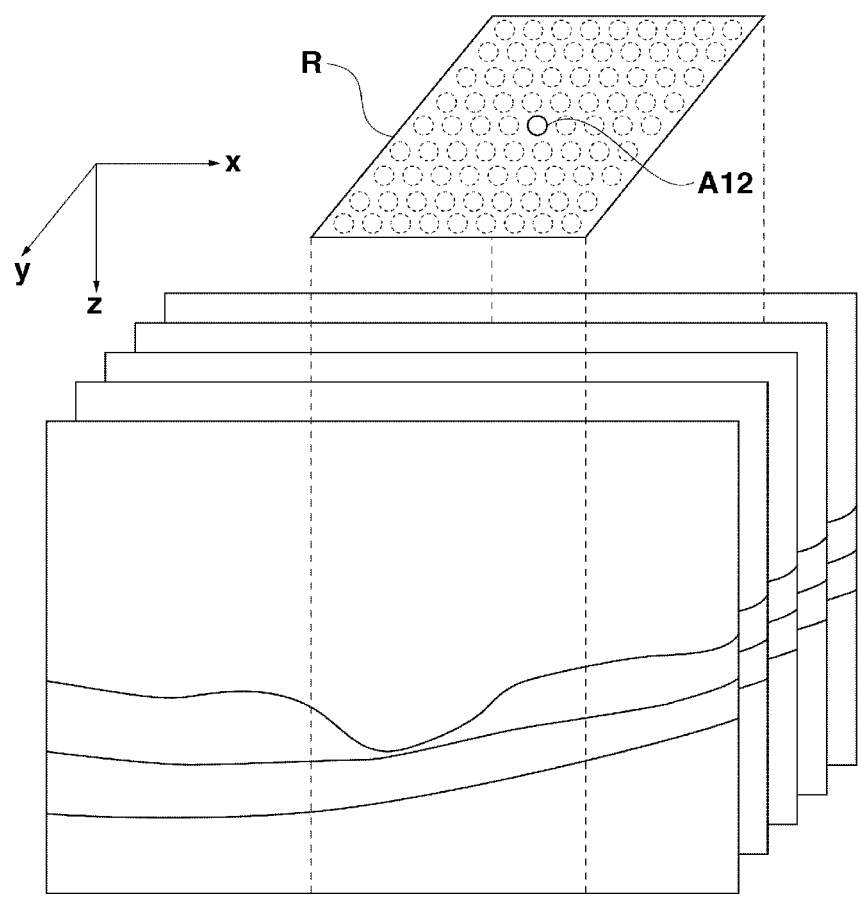
FIG. 12 schematically illustrates example processing that can be performed by the layer boundary interpolation unit according to the first exemplary embodiment of the present invention.

Similar to step S1103, in the feature quantity calculation, the A-scan line along which the position of the retinal layer boundary was not identified is located at the center of the neighborhood area set by the layer boundary interpolation unit 109, as illustrated in FIG. 12. The layer boundary interpolation unit 109 obtains an average z-coordinate value of each retinal layer boundary identified in the neighborhood area and designates the obtained z-coordinate position as a feature quantity.

Similar to step S1102, the layer boundary interpolation unit 109 determines whether to perform the feature quantity calculation processing by checking whether the total number of the A-scan lines along which the retinal layer boundary has already been identified in the neighborhood area is greater than or smaller than a predetermined number.

The layer boundary interpolation unit 109 sets a search range for each retinal layer boundary referring to the average z-coordinate value of the retinal layer calculated as the above-described feature quantity. The search range set by the layer boundary interpolation unit 109 is a predetermined range including the average z-coordinate value positioned at the center thereof. In the present exemplary embodiment, the predetermined range is composed of five pixels positioned on the front side of the average z-coordinate value and five pixels positioned on the rear side of the average z-coordinate value.

(Step S2106) The layer boundary interpolation unit 109 searches for a peak appearing on the profile of the Sobel image B in the search range. If at least one peak is present, the layer boundary interpolation unit 109 identifies a largest peak that is equal to or greater than a predetermined threshold value as a retinal layer boundary. If two or more peaks are present, the layer boundary interpolation unit 109 identifies a peak whose position is closest to the calculated average Z-coordinate value as the position of a target layer boundary.

More specifically, two or more layer boundaries may be included in a search range set to identify a layer boundary. In such a case, the layer boundary interpolation unit 109 selects a peak whose position is closest to an average depth value of the already identified layer boundary in the neighborhood area. Thus, each layer boundary can be accurately identified.

Figure 22:
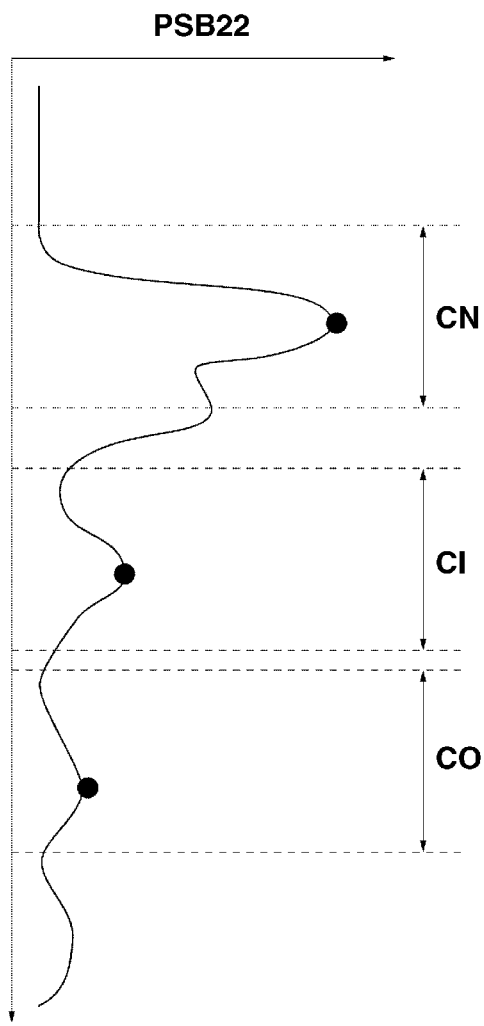
FIG. 22 illustrates an example of search range setting that can be performed by the layer boundary interpolation unit according to a fourth exemplary embodiment of the present invention.

FIG. 22 illustrates an example profile PSB220 of the Sobel image B, taken along an A-scan line extending in an area where three layers of the nerve fiber layer, the inner plexiform layer, and the outer plexiform layer are present. The profile PSB220 illustrated in FIG. 22 includes four peaks because one of the peaks is a noise. In this case, it is difficult to identify each retinal layer boundary depending on the magnitude of each peak.

However, it is feasible to accurately identify each retinal layer boundary by using a search range CN of the nerve fiber layer boundary, a search range CI of the inner plexiform layer boundary, and a search range CO of the outer plexiform layer boundary, which can be set in step S2104 based on the average z-coordinate value calculated in the neighborhood area.

As described above, even when a plurality of peak positions are discovered, the retinal layer boundary identification processing can be accurately performed by identifying a peak position closest to an already identified average z-coordinate value as the position of a target layer boundary.

(Another Exemplary Embodiment) The image processing apparatus described in each exemplary embodiment is a mere example that can realize the present invention. However, the present invention is not limited to the image processing apparatus. Further, a comparable software configuration is employable to realize the image processing apparatus 101 described in each of the first to fourth exemplary embodiments.

In this case, a storage medium storing a program that causes a computer to execute the processing of the image processing apparatus 101 according to each of the above-described exemplary embodiments can be supplied to a system or an apparatus. Then, a computer (or a CPU or a microprocessing unit (MPU)) installed in the system or the apparatus can read a program code from the storage medium and execute the read program so as to realize the present invention. In this case, the program code itself read from the storage medium realizes the functions of the above-described exemplary embodiments. The storage medium storing the program code constitutes the present invention.

In the above-described exemplary embodiments, the image processing apparatus performs analysis processing on three-dimensional image data composed of a plurality of tomography images to be acquired. However, it may also be useful that the image processing apparatus selects a two-dimensional tomography image to be concerned from the three-dimensional image data and performs processing on the selected tomography image.

For example, it may be useful that the image processing apparatus performs processing on a tomography image including a specific portion (e.g., central pit) of the ocular fundus. In this case, each detected layer boundary can be obtained as two-dimensional data that reflect the above-described cross section.

In the above-described exemplary embodiments, the image processing apparatus identifies each layer boundary. However, the image processing apparatus may identify the type and the position of each layer using template information. In this case, the image processing apparatus requires, as the template information, information relating to the magnitude (or luminance value) of a luminance change at the edge corresponding to the position of each layer boundary, or luminance values or its relationship in the magnitude between respective layer areas.

For example, macula, optic disc, retinal area including a blood vessel, and retinal area including no blood vessel can be regarded as template information.

Further, the image processing apparatus can identify a layer structure of the macula or the optic disc based on the total number of layer boundaries and a luminance value of each layer area. For example, the image processing apparatus can determine whether a target layer is the macula, the optic disc, or another area, such as an area where a blood vessel is present, an area where a leucoma is present, or an area where retina detachment is present.

Further, the image processing apparatus can determine whether a retinal layer structure includes a pseudo-image of a blood vessel or a leucoma as a feature that can be recognized in a tomography image.

The layer boundary interpolation processing according to the above-described exemplary embodiment can be performed independently from the above-described layer boundary identification processing to be performed based on template information. For example, the above-described layer boundary interpolation processing can be employed in a case where a layer boundary is partly identified using another method.

The tomography image to be used in the above-described exemplary embodiment is not limited to a tomography image of retinal layers and can be a tomography image of an anterior ocular portion. The anterior ocular portion has a multilayered structure that is composed of a cornea, a lens, and a vitreous body, which are sequentially disposed in the incident direction of signal light, i.e., in the depth direction.

Therefore, the present invention can be applied to a tomography image of the anterior ocular portion. In this case, the storage unit 111 stores a plurality of templates that represent a plurality of structures in the profile of the tomography image of the anterior ocular portion.

The image processing system 100 described in the above-described exemplary embodiment is an example to which the present invention can be applied. The optical coherence tomography imaging apparatus can be configured to have the above-described functions of the image processing apparatus 101.

Further, in the above-described exemplary embodiments, the example tomography image is a tomography image obtained by the optical coherence tomography imaging apparatus. The present invention can be applied to a tomography image obtained by an ultrasonic tomography imaging apparatus or a comparable apparatus capable of imaging an internal structure of a target to be captured.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-064755 filed Mar. 19, 2010, which is hereby incorporated by reference herein in its entirety.

The invention claimed is:

1. An image processing apparatus comprising:
an acquisition unit configured to acquire a tomography image of a target to be captured;
a detection unit configured to detect layer boundaries of a plurality of layers sequentially positioned in the depth direction from the acquired tomography image;
a calculation unit configured to calculate the number of the layer boundaries of the plurality of layers sequentially positioned in the depth direction at a predetermined position of the image; and
a determination unit configured to determine each type of the detected layer boundaries of the target to be captured according to the number calculated by the calculation unit,
wherein the determination unit is configured to determine the structure of a target eye to be captured by at least one of:
checking the type of the layer boundaries at a predetermined horizontal position of the tomography image,
checking the position of the layer boundaries at a predetermined horizontal position of the tomography image,
checking the type of layers at a predetermined horizontal position of the tomography image,
checking the presence of a pseudo-image at the predetermined position, and
determining whether the predetermined position corresponds to at least one of the macula of the retina, the optic disc of the retina, and other portion of the retina, and a combination thereof.

2. The image processing apparatus according to claim 1, wherein the determination unit is configured to determine the type of layer boundaries at a predetermined horizontal position of the tomography image according to the number of the detected layer boundaries at the predetermined position.

3. The image processing apparatus according to claim 2, further comprising:
a selection unit configured to select at least one template information from a plurality of types of template information that represent the type of layer boundaries sequentially positioned in the depth direction at a plurality of positions of the target to be captured, based on the number of the detected layer boundaries at the predetermined position,
wherein the determination unit is configured to identify the type of layer boundaries at the predetermined position based on the selected template information and the detected layer boundaries.

4. The image processing apparatus according to claim 3, wherein the selection unit is configured to select the template information from a plurality of types of template information stored in a storage unit in association with the number of layer boundaries of the target to be captured.

5. The image processing apparatus according to claim 3, wherein at least one of the plurality types of the template information includes information indicating the type of layer boundaries in a retinal area where a macula, an optic disc, or a blood vessel is present as the target to be captured or in a retinal area where no blood vessel is present.

6. The image processing apparatus according to claim 1, wherein the determination unit is configured to determine the structure of the target to be captured based on the number of the detected layer boundaries and a luminance value of a layer area between the layer boundaries.

7. The image processing apparatus according to claim 6, wherein the determination unit comprises a determination unit configured to determine the type of the layer boundaries based on the number of layer boundaries detected at a predetermined horizontal position of the tomography image and the luminance value of the layer area between the layer boundaries.

8. The image processing apparatus according to claim 7, further comprising:
a selection unit configured to select at least one piece of template information from a plurality of types of template information that represent the type of layer boundaries sequentially positioned in the depth direction at a plurality of positions of the target to be captured, based on the number of the layer boundaries detected at the predetermined position,
wherein the template information selected by the selection unit includes information relating to the position and the type of layer boundaries sequentially positioned in the depth direction of the tomography image and information relating to the luminance value of the layer area, and the template information is stored in a storage unit in association with the number of layer boundaries.

9. The image processing apparatus according to claim 8, wherein the selection unit is configured to select the template information according to the number of the detected layer boundaries, and determine whether the selected template match the predetermined position with reference to information relating to the luminance value of the layer area included in the selected template information and information relating to a row of pixels disposed in the depth direction at the predetermined position, and includes
an identifying unit configured to identify the type of layer boundaries at the predetermined position based on the selected template information and the detected layer boundaries.

10. The image processing apparatus according to claim 9, wherein the selection unit is configured to cancel the layer boundary identification processing if it is determined that the selected template does not match the predetermined position.

11. The image processing apparatus according to claim 8, wherein the selection unit is configured to select at least one piece of template information from a plurality of types of template information based on a similarity between luminance information of a row of pixels disposed in the depth direction at a predetermined horizontal position of the acquired tomography image and information relating to the luminance value of the layer area included in the template information.

12. The image processing apparatus according to claim 8, wherein the template information includes information indicating a luminance value in the vicinity of an edge position in the depth direction at the predetermined position and information indicating the type of a layer boundary that corresponds to the edge position.

13. The image processing apparatus according to claim 1, further comprising a generation unit configured to generate a profile that represents a relationship between depth directional position and luminance in a predetermined horizontal position of the tomography image from the tomography image,
wherein the detection unit is configured to acquire edges that are greater than a predetermined threshold in the depth direction of the tomography image based on the generated profile and identify the position of the layer boundaries based on the acquired edges.

14. The image processing apparatus according to claim 1, wherein the acquisition unit is configured to acquire the tomography image of the target, which can be captured by an optical coherence tomography imaging apparatus.

15. An image processing apparatus comprising:
an acquisition unit configured to acquire a tomography image of an eye;
a storage unit configured to store the number of edges detectable in the depth direction at a plurality of horizontal positions of the tomography image of the eye in association with the type of layer boundaries corresponding to the edges;
a detection unit configured to detect edges from a row of pixels disposed in the depth direction at predetermined horizontal positions of the acquired tomography image;
a calculation unit configured to calculate the number of the edges disposed in the depth direction at a predetermined position of the image; and
an identifying unit configured to identify the type of layer boundaries that correspond to the detected edges with reference to the number of the detected edges and the stored information.

16. An image processing apparatus comprising:
a generation unit configured to generate a profile that represents a relationship between depth directional position and luminance at a predetermined horizontal position of a tomography image of an eye;
a selection unit configured to select, based on the generated profile, template information that matches the predetermined horizontal position from template information including information representing a relationship between depth directional position and luminance at a plurality of horizontal positions of the tomography image and information relating to the type and the position of layer boundaries; and
an identifying unit configured to determine each type of layer boundaries detected at the predetermined position based on the generated profile with reference to the selected template information.

17. An image processing apparatus comprising:
an acquisition unit configured to acquire edges detectable in the depth direction at a predetermined horizontal position of a tomography image of an eye;
a calculation unit configured to calculate the number of the edges disposed in the depth direction at a predetermined position of the image;
a determination unit configured to determine each type of detected layer boundaries of a target to be captured according to the number calculated by the calculation unit; and
an identifying unit configured to identify the type of layers sequentially positioned in depth direction at the predetermined horizontal position based on the number of acquired edges,
wherein the determination unit is configured to determine the structure of a target eye to be captured by at least one of:
checking the type of the layer boundaries at a predetermined horizontal position of the tomography image,
checking the position of the layer boundaries at a predetermined horizontal position of the tomography image,
checking the type of layers at a predetermined horizontal position of the tomography image,
checking the presence of a pseudo-image at the predetermined position, and
determining whether the predetermined position corresponds to at least one of the macula of the retina, the optic disc of the retina, and other portion of the retina, and a combination thereof.

18. An image processing system comprising:
an optical coherence tomography imaging unit;
a detection unit configured to detect layer boundaries of a plurality of layers sequentially positioned in the depth direction from a tomography image of an eye captured by the optical coherence tomography imaging unit;
a calculation unit configured to calculate the number of the layer boundaries of the plurality of layers sequentially positioned in the depth direction at a predetermined position of the image; and
a determination unit configured to determine each type of the detected layer boundaries of the eye according to the number of the detected layer boundaries of the plurality of layers sequentially positioned in the depth direction at the predetermined position of the image; and
a display unit configured to display the tomography image together with the determined layer boundaries in a display pattern in accordance with a type of the layer boundaries.

19. A computer-readable storage medium storing a program that causes a computer to execute image processing, the program comprising:
computer-executable instructions for acquiring a tomography image of an eye;
computer-executable instructions for detecting layer boundaries of a plurality of layers sequentially positioned in the depth direction from the acquired tomography image; and
computer-executable instructions for calculating the number of the layer boundaries of the plurality of layers sequentially positioned in the depth direction at a predetermined position of the image; and
computer-executable instructions for determining each type of the detected layer boundaries of the eye according to the number of the detected layer boundaries calculated by the calculation unit,
wherein the determination unit is configured to determine the structure of a target eye to be captured by at least one of:
checking the type of the layer boundaries at a predetermined horizontal position of the tomography image,
checking the position of the layer boundaries at a predetermined horizontal position of the tomography image,
checking the type of layers at a predetermined horizontal position of the tomography image,
checking the presence of a pseudo-image at the predetermined position, and
determining whether the predetermined position corresponds to at least one of the macula of the retina, the optic disc of the retina, and other portion of the retina, and a combination thereof.

20. An image processing method comprising:
causing an acquisition unit to acquire a tomography image of an eye;
causing a detection unit to detect layer boundaries of a plurality of layers sequentially positioned in the depth direction from the acquired tomography image;

causing a calculation unit to calculate the number of the layer boundaries of the plurality of layers sequentially positioned in the depth direction at a predetermined position of the image; and causing a determination unit to determine each type of the detected layer boundaries of the eye according to the number of the detected layer boundaries calculated by the calculation unit, wherein the determination unit is configured to determine the structure of a target eye to be captured by at least one of:

checking the type of the layer boundaries at a predetermined horizontal position of the tomography image, checking the position of the layer boundaries at a predetermined horizontal position of the tomography image, checking the type of layers at a predetermined horizontal position of the tomography image, checking the presence of a pseudo-image at the predetermined position, and determining whether the predetermined position corresponds to at least one of the macula of the retina, the optic disc of the retina, and other portion of the retina, and a combination thereof.

* * * * *